US006998106B1

(12) United States Patent
Zalutsky

(10) Patent No.: US 6,998,106 B1
(45) Date of Patent: Feb. 14, 2006

(54) RADIOCONJUGATION OF INTERNALIZING ANTIBODIES

(75) Inventor: Michael R. Zalutsky, Chapel Hill, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 09/203,676

(22) Filed: Dec. 1, 1998

(51) Int. Cl.
A61K 51/08 (2006.01)
A61K 51/10 (2006.01)
A61K 38/02 (2006.01)
A61K 39/44 (2006.01)

(52) U.S. Cl. .................. 424/1.53; 424/179.1; 514/5; 530/300; 530/391.5

(58) Field of Classification Search ............. 530/388.1, 530/388.22, 389.7, 300, 391.5; 424/179.1, 424/1.37, 1.53; 514/5
See application file for complete search history.

(56) References Cited

U.S. PATENT DOCUMENTS

| 4,614,723 A | * | 9/1986 | Schmidt et al. ............. 436/536 |
| 4,885,153 A | | 12/1989 | Wilbur et al. |
| 5,130,116 A | * | 7/1992 | Woo et al. .................. 424/1.49 |
| 5,302,700 A | | 4/1994 | Zalutsky et al. |
| 5,541,297 A | | 7/1996 | Hansen et al. |

FOREIGN PATENT DOCUMENTS

| WO | WO 90/09162 | * | 8/1990 |
| WO | WO 98/08548 | | 3/1998 |
| WO | WO 99/11294 | | 3/1999 |

OTHER PUBLICATIONS

Emery et al, "Strategies for Humanizing Antibodies" in Antibody Engineering, 2nd Edition, Carl A. Borrebaeck, Ed., pp. 159-183, 1995.*
Kindzelskii et al, "Imaging the Spatial Distribution of Membrane Receptors during Neutrophil Phagocytosis." Journal of Structural Biology, vol. 113, pp. 191-198, 1994.*
Miller et al, "Proteolytic Studies of Homologous Peptides and N-Substituted Gylcine Peptoid Oligomers." Bioorganic & Medicinal Chemistry Letters, vol. 4, No. 22, pp 2657-2662, 1994.*
Mathews and Van Holde, Biochemistry (textbook), 2nd edition, pp. 165-171.*
Bowie et al, "Deciphering the Message in Protein Sequences . . . " Science, vol. 247, pp. 1306-1310.*
Derwent Accession No. 1994-026637, Barnett et al, CA 2094658A, Oct. 24, 1993. (abstract).*
Abstract of Reist et al (Cancer research, 1995, vol. 55, pp. 4375-4382).*
Abstract of Wikstrand et al (Cancer Research, Sep. 1997, vol. 57, pp. 4130-4140).*
Schlom (In: Molecular Foundations of Oncology, 1991, pp. 95-134).*
Michael R. Zalutsky, "Astatine and Iodine Radiolabeled Monoclonal Antibodies" CRISPAbstract to NIH Grant 5R01CA42324-12 (published Jun. 24, 1994) <http://commons.cit.nih.gov/crisp_historical/owa/crisp_lib.getdoc?-textkey=2330729&p_grant_num=5R01CA42324-12&p_query=&ticket=130238&p_audit_session_id=57936&p_keywords=>.
"Immunomedics Awarded U.S. Patent for Therapeutic Conjugates of Toxings and Drugs Immunomedics Invents New Targeted Therapies for Cancers and Infectious Diseases" PR Newswire via Individual, Inc., Aug. 14, 1996.
C.J. Reist et al. "Radioiodination of internalizing monoclonal antibodies using N-succinimidyl 5-iodo-3-pyridinecarboxylate" Cancer Res. 1996 No. 1;56(21 :4970-7 Nov. 1, 1996.
C.J. Reist et al. "In Vitro and In Vivo Behavior of Radiolabeled Chimeric Anti-EGFRvIII Monoclonal Antibody: Comparison with its Murine Patent" Nuclear Medicine & Biology, vol. 24, pp. 639-647 1997.
S.R. Govindan et al. "A non-metabolizable TPA-peptide (DPEP) approach for production of a residualizing Iodine radiolabeled for targeting human lung cancer xenografts" Proceedings of the American Association for Cancer Research, vol. 39, Mar. 1996 #2585 (Abstract).
S.V. Govindan et al. "Peptide-based Residualizing Radioiodine Labels for Radioimmunotherapy" Journal of Nuclear Medicine, vol. 39, No. 5, May 1998 No. 989 (Abstract).
C.J. Reist et al. "Improved Targeting of an Anti-Epidermal Growth Factor Receptor Variant III Monoclonal Antibody in Tumor Xenografts after Labeling Using N-Succinimidyl 5-Iodo-3-Pyridinecarboxylate" Cancer Research 57, 1510-1515 Apr. 15, 1997.
S.V. Govindan, et al., "Labeling of Monoclonal Antibodies with Diethylenetriaminepentaacetic Acid-Appended Radionated Peptides Containing D-Amino Acids", Bioconjugate Chemistry, 1999 Mar.-Apr. 10 (2) 231-240.

(Continued)

Primary Examiner—Karen A. Canella
(74) Attorney, Agent, or Firm—Banner & Witcoff, Ltd.

(57) ABSTRACT

Antibodies to cell surface ligands such as EGFRvIII can be used to therapeutically or diagnostically deliver a radiolabel to tumor cells with high selectivity. The utility of radioconjugated internalizing antibodies is limited, however, by release of the label and its reuptake into normal cells. The invention provides new technology for radioconjugation of internalizing antibodies which reduces the release of label and improves retention of radioconjugated antibodies in lysosomes, where radiation is more effectively and selectively delivered to the nucleus of tumor cells.

25 Claims, 6 Drawing Sheets

OTHER PUBLICATIONS

M. R. Zalutsky, et al., "Radioiodination Via D-Amino Acid Peptide Enhances Tumor Targeting of an Internalizing Anti-EGFRvIII Monoclonal Antibody", Proceedings of the American Association for Cancer Research Annual Meeting, Mar. 2000, No. 41, pp. 706.

Y. Arano, et al., "Conventional and High Yield Synthesis of DTPA-Conjugated Peptides: Application of a Monoreactive DTPA to DTPA-D-Phe-Octreotide Synthesis", Bioconjugate Chemistry, vol. 8, 1997, pp. 442-446.

T. M. Behr, et al., "Reduction of the Renal Uptake of Radiolabeled Monoclonal Antibody Fragments by Cationic Amino Acids and Their Derivatives", Cancer Research, US, American Association for Cancer Research, Baltimore, MD, vol. 55, Sep. 1, 1995, pp. 3825-3834.

K. Zimmermann, et al., "A Triglycine Linker Improves Tumor Uptake and Biodistributions of 67-Cu-Labeled Anti-Neuroblastoma MAbchCE7 F(ab')2 Fragments—Reactivity Studies of the Pendant Carboxylic Group in a Macrocyclic Cu2+ Complex Towards Amide Formation and its Use as a Protein Labeling Agent", Nuclear Medicine and Biology, US, Elsevier Science Publishers, New York, NY, vol. 26, No. 8, Nov. 1999, pp. 943-950.

C. F. Foulon, et al., "Radioiodination Via D-Amino Acid Peptide Enhances Cellular Retention and Tumor Xenograft Targeting of an Internalizing Anti-Epidermal Growth Factor Receptor Variant III Monoclonal Antibody", Cancer Research, vol. 60, Aug. 15, 2000, pp. 4453-4460.

M. R. Zalutsky, et al., "Astatine-211-Labeled Radiotherapeutics: an Emerging Approach to Targeted Alpha Particle Radiotherapy", Current Pharmaceutical Design, vol. 6 Sep. 2000, pp. 1433-1455.

C. J. Reist, et al., "In Vitro and In Vivo Behavior of Radiolabeled Chimeric Anti-EGFRvIII Monoclonal Antibody: Comparison with its Murine Parent", Nuclear Medicine and Biology, US, Elsevier Science Publishers, New York, NY, vol. 24, No. 7, Oct. 1, 1997, pp. 639-647.

C. J. Reist, et al., "Astatine-211-Labeling of Internalizing Anti-RGFRvIII Monoclonal Antibody Using N-Succinimidyl 5-'At!astato-3-Pyridinecarboxylate—Preservation of Immunoreactivity and in Vivo Localizing Capacity", Nuclear Medicine and Biology, US, Elsevier Science Publishers, New York, NY, vol. 26, No. 4, May 1999, pp. 405-411.

J. Sundin, et al., "High Yield Direct Br-Bromination of Monoclonal Antibodies Using Chloramine-T—Detection of Colorectal Carcinoma with Positron-Emitting Copper-64-Labeled Monoclonal Antibody", Nuclear Medicine and Biology, US, Elsevier Science Publishers, New York, NY, vol. 26, No. 8, Nov. 1999, pp. 923-929.

R. Stein, et al., "Targeting Human Cancer Xenografts with Monoclonal Antibodies Labeled Using Radioiodinated Diethylenetriaminepentaacetic Acid-Appended Peptides", Clinical Cancer Research, vol. 5, No. Suppl., Oct. 1999, pp. 3079s-3087s.

* cited by examiner

SCHEME A

SCHEME B

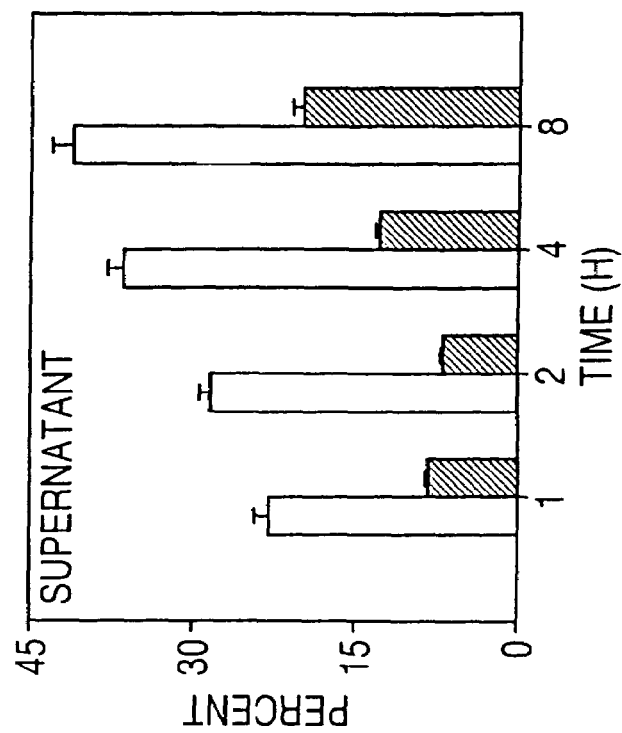
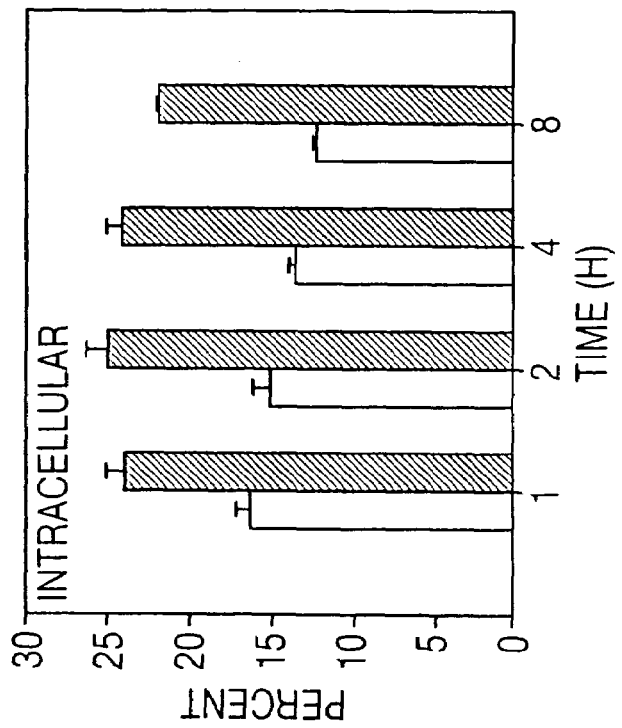

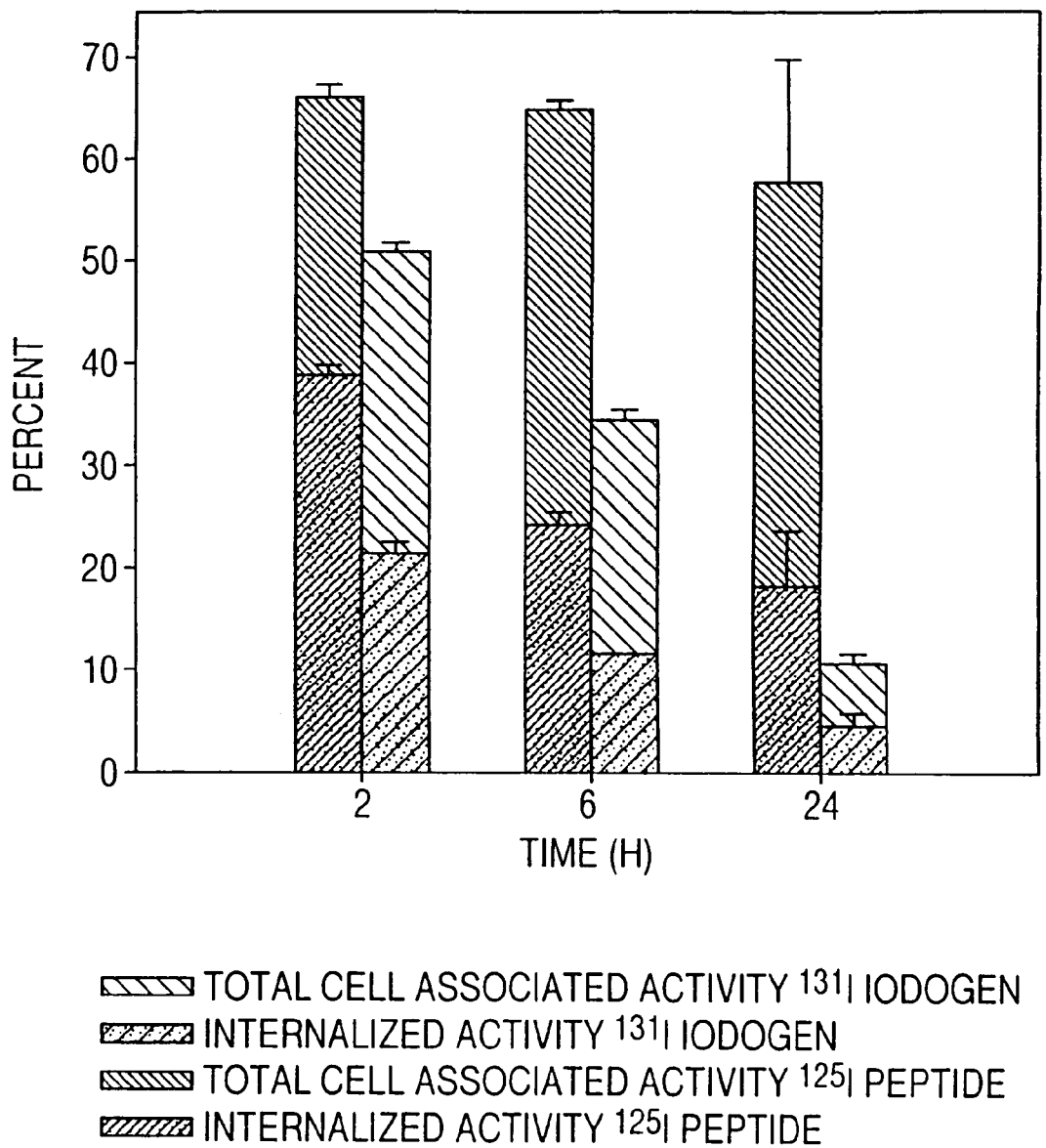

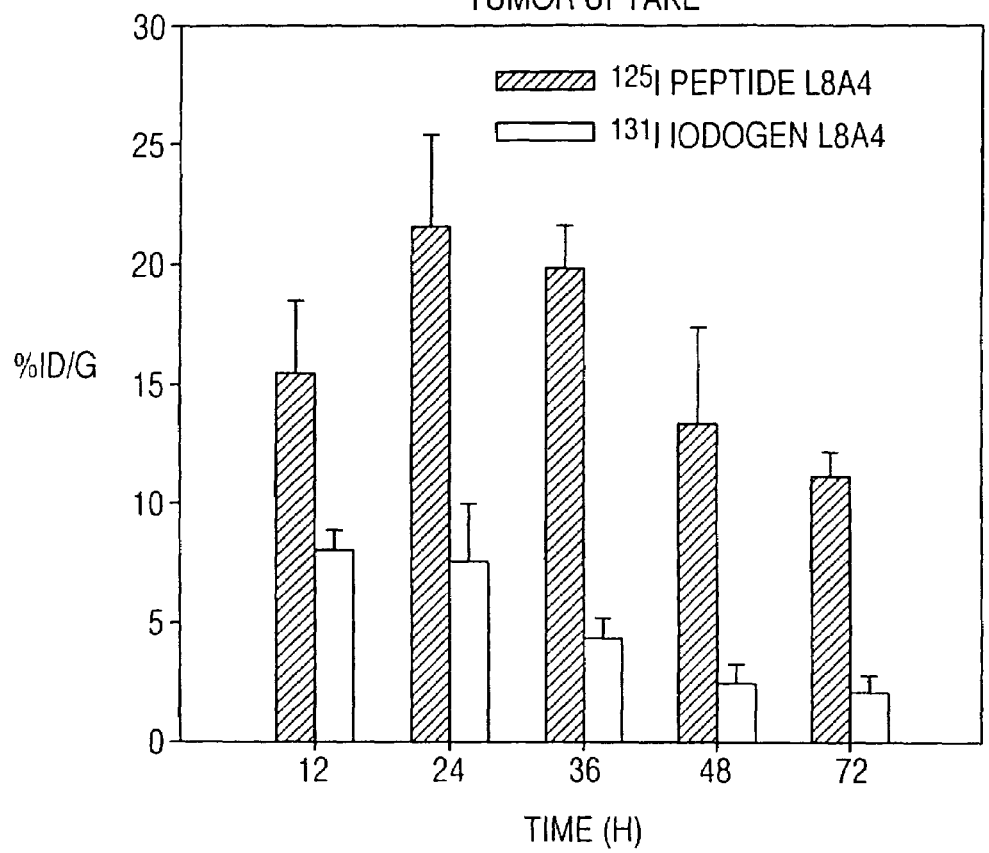

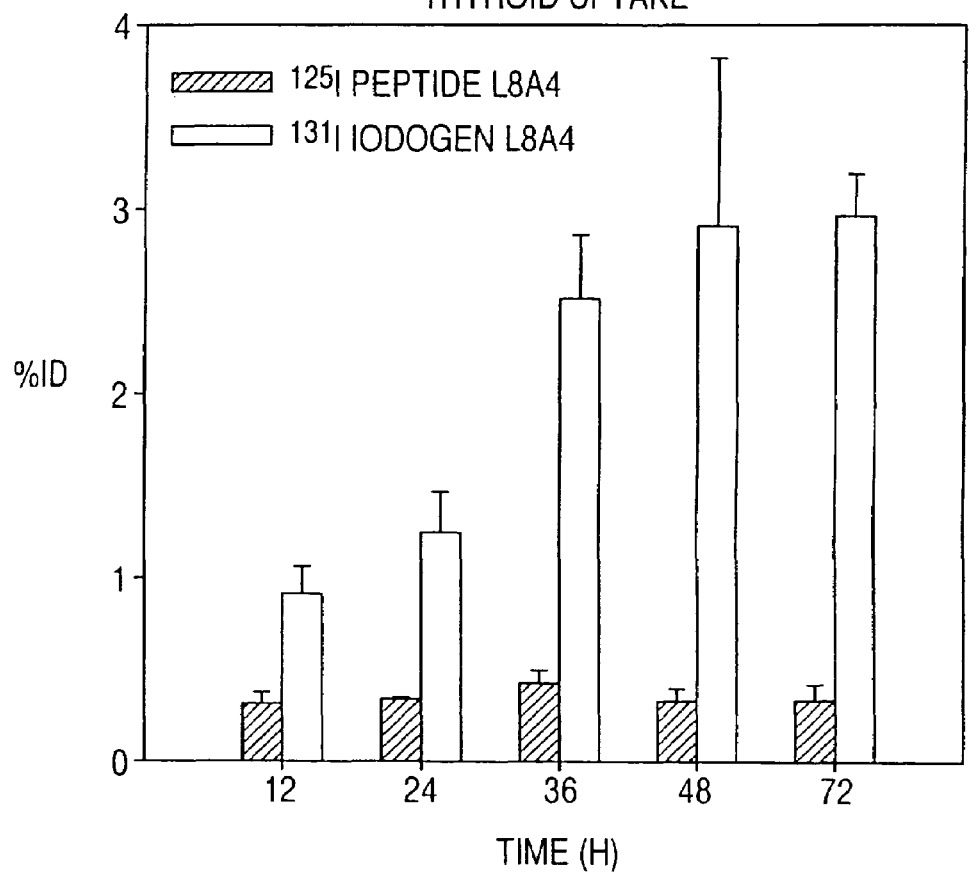

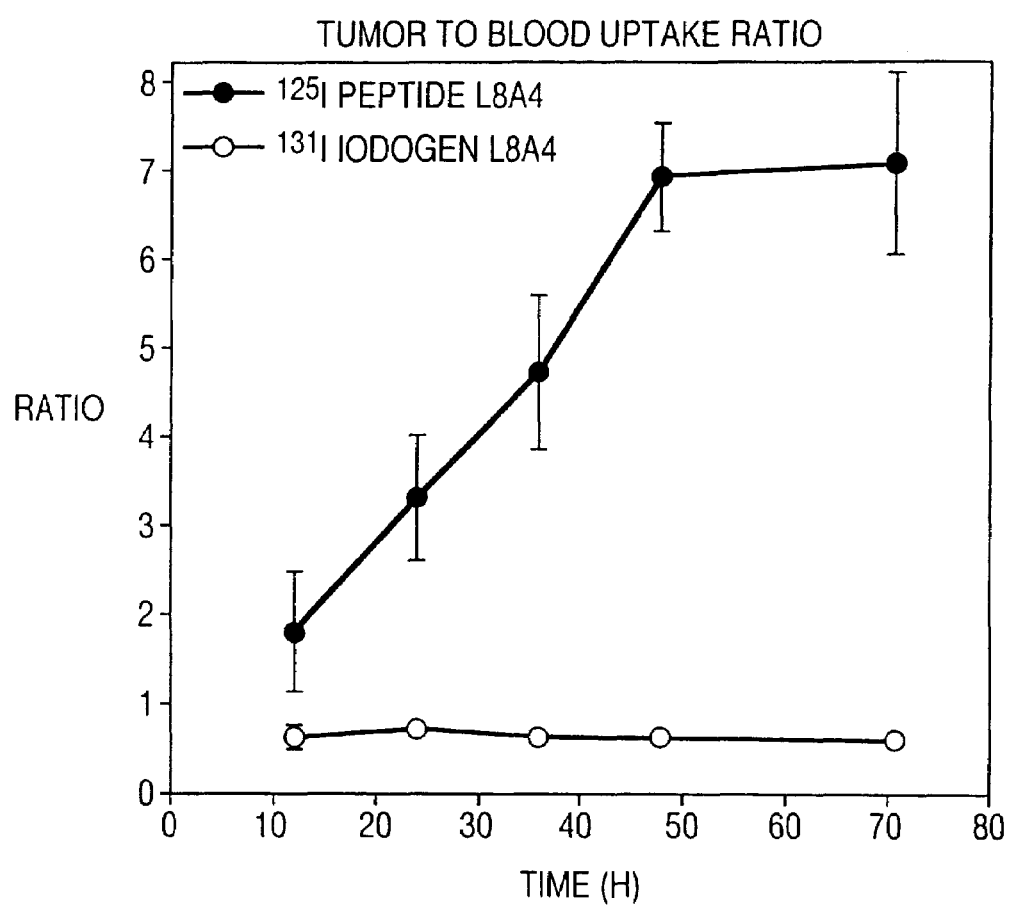

SEQUENCE LISTING

<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: Description of Artificial Sequence:
      Oligopeptide for conjugation of radiolabel to an antibody.
<220> FEATURE:
<221> NAME/KEY: MISC_FEATURE
<222> LOCATION: (1)..(4)
<223> OTHER INFORMATION: All residues are D-amino acids.

<400> SEQUENCE: 1

Lys Arg Arg Arg
1

<210> SEQ ID NO 2
<211> LENGTH: 4
<212> TYPE: PRT
<213> ORGANISM: Artificial
<220> FEATURE:
<223> OTHER INFORMATION: Description of Artificial Sequence:
      Oligopeptide for conjugation of radiolabel to an antibody.

<400> SEQUENCE: 2

Tyr Arg Arg Arg
1

<210> SEQ ID NO 3
<211> LENGTH: 5
<212> TYPE: PRT
<213> ORGANISM: Artificial
<220> FEATURE:
<223> OTHER INFORMATION: Description of Artificial Sequence:
      Oligopeptide for conjugation of a radiolabel to an antibody
<220> FEATURE:
<221> NAME/KEY: MISC_FEATURE
<222> LOCATION: (1)..(5)
<223> OTHER INFORMATION: N-terminus is acetylated.  All residues are
      D-amino acids

<400> SEQUENCE: 3

Lys Arg Tyr Arg Arg
1               5

RADIOCONJUGATION OF INTERNALIZING ANTIBODIES

The U.S. Government retains certain rights in this invention due to funding of grant CA42324 awarded by the National Institutes of Health.

TECHNICAL FIELD OF THE INVENTION

The invention is related to the area of radioconjugation technology. In particular it is related to the use of internalizing antibodies in radioimmunotherapy.

BACKGROUND OF THE INVENTION

Monoclonal antibodies (mAbs) are attractive vehicles for targeting radiation to tumors because of their ability to react specifically with molecular determinants on cancer cells. However, the anticipated impact of labeled mAbs on the clinical management of cancer has yet to be achieved; loss of label from the mAb in vivo and uptake of radioactivity in normal tissues have impeded their clinical application. Iodine-131 is the most frequently used nuclide in clinical radioimmunotherapy, but its usefulness has been compromised by in vivo dehalogenation of mAbs labeled via conventional procedures.

Radiolabeled mAbs could play an important role in the diagnosis and treatment of cancer if the molecular specificity inherent in the mAb-antigen interaction can be successfully exploited to selectively deliver radionuclides to tumors. For many types of cancer, radioimmunotherapy is an attractive alternative to external beam radiation therapy and systemically administered chemotherapy, treatments that are frequently ineffective because of dose-limiting toxicities to normal tissues. Radioimmunoscintigraphy is appealing not only for lesion detection but also as a means for determining which patients are suitable candidates for labeled mAb therapy. Numerous clinical studies have confirmed the ability of labeled mAbs to localize in both primary and metastatic cancers (reviewed in Britton and Granowska, 1996; Larson, 1995), and in patients with radiosensitive tumors, significant therapeutic responses have been obtained with $^{131}$I-labeled mAbs (Press et al., 1995; Kaminski et al., 1996). However, other tumors have proven to be less radiosensitive, presumably due to the low level of radionuclide retained in tumor and the significant accumulation of radioactivity in normal organs (Kairemo, 1996; Bast et al., 1997). There remains a need in the art for improved techniques and reagents to selectively target both therapeutic and diagnostic radiolabels to tumor cells.

SUMMARY OF THE INVENTION

It is an object of the invention to provide radioconjugated ligands and methods of their use in locating and treating tumors. These and other objects of the invention are provided by one or more of the embodiments described below.

One embodiment of the invention provides a composition for internally labeling a cell. The composition comprises a ligand, an oligopeptide, and a label. The ligand is any moiety that specifically binds to a cell surface antigen or receptor and is internalized by the cell. The ligand is selected from the group consisting of an antibody, a fragment of an antibody, and a synthetic polypeptide. The oligopeptide comprises at least one positively charged amino acid residue and at least one D-amino acid residue. The oligopeptide does not comprise two or more contiguous L-amino acid residues. The oligopeptide is covalently bound to the ligand. The label is covalently bound to the oligopeptide.

Another embodiment of the invention provides a method of incorporating a label into a cell. The method comprises the step of contacting the cell with the composition described in the previous paragraph, whereby the label is internalized by the cell.

Still another embodiment of the invention provides a method of locating tumor cells in a mammal. The method comprises the steps of introducing a diagnostically effective amount of the above composition into the body of a mammal which comprises tumor cells, scanning the body with a scintillation detector, and generating an image depicting the tumor cells in the body of the mammal.

Yet another embodiment of the invention provides a method of radiotherapy. The method comprises the step of introducing a therapeutically effective amount of the above composition into the body of a mammal comprising a tumor, whereby growth of the tumor is diminished.

A further embodiment of the invention provides a compound for labeling a ligand which binds to a cell surface antigen. The compound comprises a molecule of formula (I):

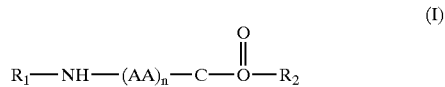

The —NH— group represents the amino end and the

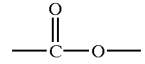

group represents the carboxyl end of the molecule. AA represents an amino acid and n is an integer having a value of at least 1 and at most about 10, 15, or 20. $R_1$ is H or an amino protecting group and $R_2$ is H or a carboxyl protecting group, with the proviso that $R_1=R_2=H$ is an unsatisfied condition for this molecule. Either $R_1$ or $R_2$ is H. At least one amino acid residue is positively charged and at least one amino acid residue is a D-amino acid. The molecule does not comprise two or more contiguous L-amino acids. At least one amino acid is sufficient to be coupled to a label. The molecule is sufficient to be coupled to a ligand at only one of its amino end or its carboxyl end.

The invention thus provides the art with novel tools to introduce labeled ligands into a cell.

BRIEF DESCRIPTION OF THE DRAWINGS

In FIG. 1A, the oligopeptide at the left (D-Lys-D-Arg-D-Arg-D-Arg, SEQ ID NO: 1) is coupled in the first reaction via the ε-amino group of D-Lys to a chemical moiety (e.g., 5-iodo-3-pyridinecarboxylate) comprising a label (e.g., $^{131}$I). In the second reaction, the free carboxyl terminus of the labeled oligopeptide is coupled to a free amino group on a monoclonal antibody. In FIG. 1B, two similar reactions are carried out, but the oligopeptide is D-Tyr-D-Arg-D-Arg-D-Arg (SEQ ID NO:2), and the label (e.g., $^{131}$I) is coupled directly to D-Tyr.

FIGS. 2A and 2B show intracellular and cell culture supernatant activity, respectively, following incubation of mAb L8A4 labaled using SIPC (solid bars) and SIB (open bars) with EGFRvIII positive HC2 20 d2 cells.

FIG. 3 depicts the binding and internalization of labeled murine L8A4 to the U87MGΔEGFR cell line, which expresses the mutant EGFRvIII receptor. The labeled antibody was prepared either by direct Iodogen labeling using $^{131}$I or using an oligopeptide (α-N-Ac-D-Lys-D-Arg-D-Tyr-D-Arg-D-Arg, SEQ ID NO:3) which had been Iodogen labeled with $^{125}$I on its D-Tyr residue and coupled to the antibody as described under Example 8.

FIG. 4 shows the time course of tumor uptake of radioiodine, expressed as the pecentage of the initial dose per gram of tumor. Murine L8A4 was labeled with $^{125}$I using the oligopeptide method and with $^{131}$I using direct Iodogen labeling. The experiment was performed in athymic mice bearing subcutaneous EGFRvIII-expressing, U87MGΔEGFR human glioma xenografts.

FIG. 5 reveals the level of thyroid accumulation of radioiodine under conditions of the experiment depicted in FIG. 3. Thyroid accumulation is an indicator of dehalogenation of radioiodinated compounds in vitro.

FIG. 6 presents the ratio of tumor-to-blood uptake of radioiodine under the conditions of the experiment depicted in FIG. 3.

DETAILED DESCRIPTION OF THE INVENTION

Figure 1:
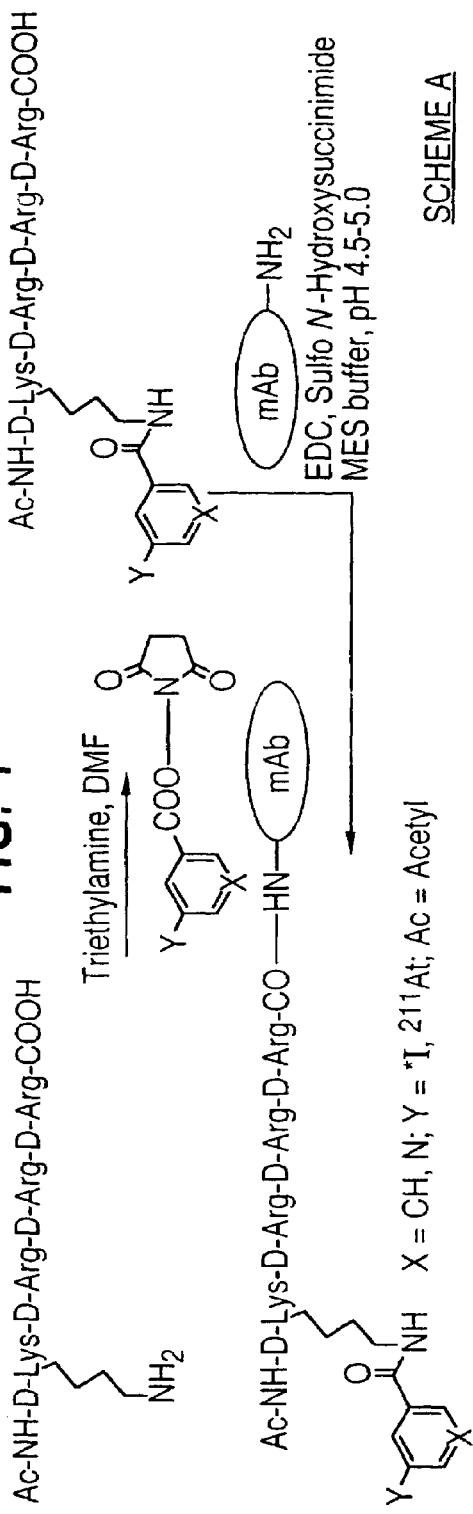
FIGS. 1A and 1B illustrate how two preferred compositions of the invention are formed.
Figure 1:
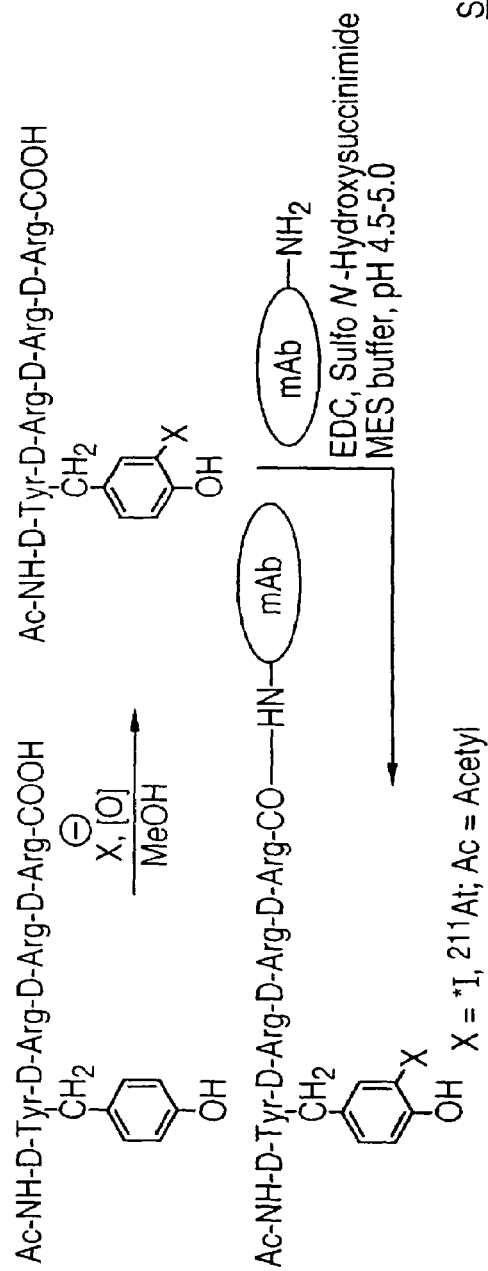

It is a discovery of the present invention that conjugation of radiolabels to ligands that bind to cell surface antigens via positively charged, proteolysis-resistant oligopeptides improves the effectiveness of radioimmunotherapy. Selective localization and retention of radiolabel within a class of target cells is increased using such oligopeptides.

A label is covalently bound to an oligopeptide comprising at least one D-amino acid residue and at least one positively charged amino acid residue. The label can be directly covalently bound to the oligopeptide, or it can be covalently bound to a chemical moiety, which in turn is covalently bound to the oligopeptide. The oligopeptide is covalently bound to the ligand.

A ligand, as the term is applied to this invention, is any molecule which specifically binds to a cell surface antigen. A cell surface antigen is any antigen or receptor on a cell surface that is internalized by the cell. Ligands can be internalized by the cell over seconds, minutes, hours, or days. Preferred ligands of the invention are internalized rapidly, i.e., most of the ligand is internalized after minutes to hours. A ligand is considered to bind specifically when it binds with an affinity constant of $10^6$ M$^{-1}$ or more, preferably $10^8$ M$^{-1}$ or more. If the cell surface antigen is a receptor, then the receptor can be internalized either with or without a bound ligand. An example of an internalizing receptor is the epidermal growth factor receptor (EGFR), which is a cell surface antigen that is internalized by the process of receptor-mediated endocytosis. Antigens or receptors which are internalized by the cell can eventually become localized within endosomes or lysosomes.

A ligand can be an antibody, a fragment of an antibody, or a synthetic peptide that binds specifically to a cell surface antigen. In a preferred embodiment the ligand is an internalizing antibody. Any antibody that specifically binds to a cell surface antigen and is internalized by the cell is an internalizing antibody. The antibody can be an immunoglobulin of any class, i.e., IgG, IgA, IgD, IgE, or IgM, and can be obtained by immunization of a mammal such as a mouse, rat, rabbit, goat, sheep, primate, human or other suitable species. The antibody can be polyclonal, i.e., obtained from the serum (also called antiserum) of an animal immunized with a cell surface antigen or fragment thereof. The antibody can also be monoclonal, i.e., formed by immunization of a mammal using the cell surface ligand or antigen or a fragment thereof, fusion of lymph or spleen cells from the immunized mammal with a myeloma cell line, and isolation of specific hybridoma clone, as is known in the art. Examples of internalizing monoclonal antibodies which are suitable for use in the invention include L8A4, Y10, and H10 (Reist et al., 1995). The antibody can also be a recombinant antibody, e.g., a chimeric or interspecies antibody produced by recombinant DNA methods. A preferred internalizing antibody is a humanized antibody comprising human immunoglobulin constant regions together with murine variable regions which possess specificity for binding to a cell surface antigen (see, e.g., Reist et al., 1997). If a fragment of an antibody is used, the fragment should be capable of specific binding to a cell surface antigen. The fragment can comprise, for example, at least a portion of an immunoglobulin light chain variable region and at least a portion of an immunoglobulin heavy chain variable region. A ligand can also be a synthetic polypeptide which specifically binds to a cell surface antigen. For example, the ligand can be a synthetic polypeptide comprising at least a portion of an immunoglobulin light chain variable region and at least a portion of an immunoglobulin heavy chain variable region, as described in U.S. Pat. No. 5,260,203 or as otherwise known in the art.

The oligopeptide comprises at least one positively charged amino acid and at least one D-amino acid. The positively charged amino acid can be either a D- or an L-amino acid. Positively charged amino acids used in the oligopeptide are those which carry a net positive charge on their side chain at the pH of the extracellular medium (about 7.4) or at the pH of the intracellular medium (about 6.8–7.2) or preferably at the pH of the lumenal contents of endosomes (about 5–6) or lysosomes (about 5). Examples of such positively charged amino acids are histidine, more preferably lysine, and most preferably arginine. Amino acids having the D-stereoisomer configuration are preferred for use in the oligopeptide, although amino acids having the L-configuration can also be used. D-amino acids render the oligopeptide more resistant to lysosomal proteases (Ehrenreich and Cohn et al., 1969), thereby improving retention of the label within the target cells and limiting release of the label and its subsequent reuptake by other cells. The oligopeptide does not contain two or more contiguous L-amino acids. In a preferred embodiment, if the oligopeptide comprises two or more L-amino acids, the L-amino acids are separated from one another by one or more positively charged amino acids. In another preferred embodiment, the oligopeptide comprises at least one D-Tyr residue. In yet another preferred embodiment, the oligopeptide comprises at least one D-Lys residue.

Any label can be used which enables the cells that take up the composition to be detected or to be affected by the label. For example, to enable detection of a group of target cells, the label can be fluorescent or radioactive. A fluorescent label or tag can also be used when specific target cells will be detected outside the body, i.e., ex vivo. Any fluorescent molecule can be used which is suitable for detection by standard methods, including, for example, fluorescence spectroscopy and fluorescence microscopy. A radioactive label or tag can be used when the cells will be detected inside or outside the body, i.e., in vivo or ex vivo. Detection can be performed by standard radiological methods, including, for example, scanning the body with a scintillation detector (radioscintigraphy) and positron emission tomography (PET) (see, e.g., Bradwell et al., 1985). For in vivo use the label should be a pharmacologically acceptable label and should be given in either diagnostically or therapeutically acceptable amounts. A therapeutically acceptable amount is an amount which, when given in one or more dosages, produces the desired therapeutic effect, e.g., shrinkage of a tumor, with a level of toxicity acceptable for clinical treatment. Both the dose of a particular composition and the means of administering the composition can be determined based on specific qualities of the composition, the condition, age, and weight of the patient, the progression of the particular disease being treated, and other relevant factors. If the composition contains antibodies, effective dosages of the composition are in the range of about 5 μg to about 50 μg/kg of patient body weight, about 50 μg to about 5 mg/kg, about 100 μg to about 500 μg/kg of patient body weight, and about 200 to about 250 μg/kg. A diagnostically acceptable amount is an amount which permits detection of the label as required for diagnosis, with a level of toxicity acceptable for diagnosis. Radiolabels that are intended for the purpose of detecting target cells should preferably emit radiation that is detectable from outside the body, e.g., gamma radiation, when given in diagnostically acceptable amounts. Such radiolabels include, but are not limited to, the radionuclides $^{18}$F, $^{76}$Br, $^{75}$Br, $^{123}$I, $^{124}$I, $^{125}$I, and $^{131}$I. Radiolabels that are intended to diminish the growth of a tumor should preferably emit radiation which is absorbed within the tumor cell so as to damage the cell, for example by disrupting the cell's DNA. Such radiolabels preferably should cause minimal damage to neighboring healthy cells. Cell-disrupting radiolabels can, for example, emit alpha, beta, and/or gamma radiation. Such radiolabels include, but are not limited to, the radionuclides $^{18}$F, $^{75}$Br, $^{76}$Br, $^{77}$Br, $^{123}$I, $^{124}$I, $^{125}$I, $^{131}$I, and $^{211}$At. Radiolabels can be covalently attached to the oligopeptide by any means known in the art, including iodination of a tyrosine residue (see, e.g., Fraker and Speck, 1978), iododestannylation (Zalutsky and Narula, 1987), and astatodestannylation (see Example I and Foulon et al., 1998).

The label can be a chemical moiety that is covalently attached to the oligopeptide. The chemical moiety has the structure of formula (II). For the chemical moiety in formula (II), X can be an amino group, a carboxyl group, or $(CH_2)_n$SH, wherein n is an integer from 0 to 10. Y can be C or N, and Z can be F, Br, I, At, or M(Alk)$_3$, wherein M can be Si, Sn, or Hg, and wherein Alk is an alkyl group such as methyl, ethyl, propyl, butyl, pentyl, or hexyl. The chemical moiety can be a carboxylic acid compound attached to an amino group on the oligopeptide. Alternatively, the chemical moiety can be an amino compound attached to a carboxyl group on the oligopeptide. Preferred carboxylic acid compounds are, for example, 5-iodo-3-pyridinecarboxylate, 3-iodobenzoate, 3-(tri-n-butylstannyl)benzoate, 5-(tri-n-butylstannyl)-3-pyridinecarboxylate, or 5-astato-3-pyridinecarboxylate. The pyridinecarboxylate compounds are preferred because they are positively charged at lysosomal pH. D-Lys is prefered as an amino acid for the oligopeptide in this composition, because the carboxylic acid compound can be attached via the E-amino group of Lys. A radionuclide, e.g., $^{18}$F, $^{75}$Br, $^{76}$Br, $^{77}$Br, $^{123}$I, $^{124}$I, $^{125}$I, $^{131}$I, and $^{211}$At, can be incorporated into the carboxylic acid compound using methods available in the art. See Zalutsky and Narula (1987).

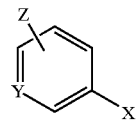

Compositions according to the invention can be used for internally labeling a cell. A label can be incorporated into a cell or group of cells by contacting the cell with a composition of the invention. As decribed in the foregoing paragraphs, a composition of the invention comprises a ligand that is covalently bound to an oligopeptide, that in turn is covalently bound to a label. The cell is contacted with the composition described above such that the label is internalized in the cell. The cell may be located within the body of a human or an animal, or it may be isolated from the body and contacted with the composition ex vivo. The composition may be contacted with the cell by any means compatible with the therapeutic or diagnostic requirements of the method. For example, the composition can be injected or infused into a patient or animal by an intravenous, subcutaneous, intramuscular, or intraperitoneal route. For in vitro application of the method, the composition can be added to the medium bathing the cell. Following internalization of the label, labeled cells can be detected using any of the methods described above. Contacting a cell with the composition means contacting the cell as often or as long as required for the purpose of analysis, diagnosis, or therapy. For example, the cell can be contacted with the composition at intervals of minutes, hours, days, weeks, months, or years.

Compounds suitable for coupling to a ligand that specifically binds to a cell surface antigen can comprise a molecule of formula (I):

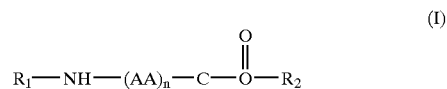

(I)

The —NH— group represents the amino end and the

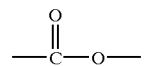

group represents the carboxyl end of the molecule. AA represents an amino acid and n is an integer having a value of at least 1. $R_1$ is H or an amino protecting group and $R_2$ is H or a carboxyl protecting group, with the proviso that $R_1=R_2=H$ is an unsatisfied condition for this molecule. Either $R_1$ or $R_2$ is H. At least one amino acid residue is a D-amino acid, and at least one amino acid residue is positively charged at lysosomal pH. The molecule does not comprise two or more contiguous L-amino acids. In a preferred embodiment, if two or more L-amino acids are used, they are separated from one another by one or more positively charged amino acid. The structure is sufficient to be coupled to a ligand at only one of its amino end or its carboxyl end.

The compounds can be labeled in a number of ways. First, an amino acid in the oligopeptide, e.g., tyrosine, can be directly iodinated. Second, a chemical moiety of formula II can be coupled to a free amino or carboxyl group on an amino acid residue of the oligopeptide, for example to the ε-amino group of D-Lys. Third, a chemical moiety of formula II can be coupled to the free amino or carboxyl end of the compound of formula I. Any method known in the art for labeling can be used. The label can be any of the labels described above. For example, the label can be a radionuclide selected from the group, $^{18}$F, $^{75}$Br, $^{76}$Br, $^{77}$Br, $^{123}$I, $^{124}$I, $^{125}$I, $^{131}$I, and $^{211}$At, or the label can be a fluorescent label. The label can be added either before or after coupling the chemical moiety of formula (II) to the oligopeptide or either before or after coupling the oligopeptide to the ligand.

The compounds can be coupled with a ligand at either their amino or carboxyl end. In order to be so coupled, they must first be protected at whichever end will not be reacted with the ligand. Free amino or carboxyl groups can be protected with any appropriate protecting group. Amino groups can be protected by conversion to an amide (see, e.g., J. March, 1977 at p. 383); the corresponding protecting group would then be, e.g., an alkylcarbonyl, arylcarbonyl, or aralkylcarbonyl group. Carboxyl groups can be protected by conversion to an ester (see, e.g., J. March, 1977, at p. 431); the corresponding protecting group would then be, e.g., an alkyl, aryl, aralkyl, or alkenyl group. Blocking groups can be added or removed by standard methods in the art.

Internalizing mAbs

Many of the known molecular targets for labeled mAbs are internalizing antigens and receptors. B-cell lymphoma (Press et al., 1994; Hansen et al., 1996), T-cell leukemia (Geissler et al., 1991) and neuroblastoma cells (Novak-Hofer et al., 1994) all possess antigens that are internalized rapidly. Clinical radioimmunotherapy trials with mAbs specific for these antigens are underway. Internalizing receptors have been used to target mAbs to tumors. These include wild-type epidermal growth factor receptor (EGFR; gliomas and squamous cell carcinoma; Brady et al., 1992; Baselga et al., 1994), the p185 c-erbB-2 oncogene product (breast and ovarian carcinomas; De Santes et al. 1992; Xu et al., 1997), and the transferrin receptor (gliomas and other tumors; Laske et al., 1997). Indeed, it has been suggested that internalization can occur with virtually any mAb that binds to a cell-surface antigen (Mattes et al., 1994; Sharkey et al., 1997a).

An advantage of mAb internalization for radioimmunotherapy is the potential for increasing the radiation absorbed dose delivered to the cell nucleus. Dosimetry calculations suggest that even with the multicellular range β-emitter $^{131}$I, shifting the site of decay from the cell membrane to cytoplasmic vesicles could increase the dose received by the cell nucleus by a factor of two (Daghighian et al., 1996). On the other hand, a disadvantage of mAb internalization is that this event exposes the mAb to additional catabolic processes that can result in the release of radioactivity from the tumor cell.

EGFRvIII—A Tumor-Specific Target

Over-expression of wild-type EGFR receptor occurs in a variety of cancers. However, EGFR is also present on many normal tissues, detracting from its merit for tumor targeting. In addition to causing overexpression, oncogenic transformation can also lead to re-arrangements of EGFR genes, including some which are characterized by deletion mutations in the receptor's extracellular domain (Wong et al., 1992). One of these, EGFRvIII, has an in-frame deletion of 801 base pairs, resulting in the removal of $NH_2$-terminal amino acids 6 to 273 and the generation of a novel glycine residue at the fusion point. This produces a 145 kDa mutant receptor, compared with 170 kDa for wild-type EGFR (Humphrey et al., 1990). Expression of EGFRvIII has been reported on the majority of gliomas, medulloblastomas, breast and ovarian carcinomas, as well as 16% of small cell lung carcinomas (Garcia de Palazzo et al., 1993; Moscatello et al., 1995; Wikstrand et al., 1995). EGFRvIII has not been found on normal tissues, including those expressing wild-type EGFR. Because EGFRvIII is only expressed in cells undergoing malignant transformation, this molecule appears to be truly tumor specific and thus of great value for diagnostic and therapeutic applications. Quantitative flow cytometry of biopsies from glioma patients has revealed an average of $3\times10^5$ to $7\times10^5$ EGFRvIII receptors per cell (Wikstrand et al., 1997), a level that should be more than sufficient for tumor targeting. Antibodies that are specific for EGFRvIII were developed using a 14-mer peptide corresponding to the fusion junction as the immunogen (Humphrey et al., 1990; Wikstrand et al., 1995). Several mAbs, including L8A4, Y10, and H10, have affinity constants ($K_A$) for binding to EGFRvIII-positive HC2 20 d2 cells of between $1.3\times10^9$ and $2.5\times10^9$ M$^{-1}$ after radioiodination (Reist et al., 1995).

The murine anti-EGFRvIII mAb L8A4 IgG1 was developed using protocols involving immunization of BALB/c mice with a synthetic peptide representing the unique EGFRvIII sequence as well as EGFRvIII-positive HC2 20 d2 cells (Wikstrand et al., 1995). This mAb specifically precipitates mutant 145-kDa EGFRvIII but not wild-type 170 kDa EGFR, and is internalized into EGFRvIII-expressing cells within 5 min of binding to the receptor (Reist et al., 1995). The affinity constant for murine L8A4 binding to the neoepitope of EGFRvIII, determined by surface plasmon resonance, is $2.0\pm1.0\times10^9$ M$^{-1}$ (Reist et al., 1997). Single chain $F_v$ (sc$F_v$) constructs based on the L8A4 variable region can also be used instead of the whole L8A4 antibody. An sc$F_v$ monomer was labeled with SIPC and found to have a $K_A$ of $1.5\times10^8$ M$^{-1}$ and an immunoreactive fraction of 65–80%. Multivalent constructs have been created by varying the length of the linker between the $V_L$ and $V_H$ domains; with a 5 amino acid linker, a dimer has been generated with a $K_A$ of $5.5\times10^9$ M$^{-1}$ measured by surface plasmon resonance.

Chimeric Antibodies

Repeated doses of murine antibodies in humans as required for optimal therapeutic efficacy lead to the development of human anti-mouse antibody responses (Tjandra et al., 1990) which may cause allergic reactions or inhibit targeting of the murine antibody to the tumor. This problem can be addressed by producing human/murine recombinant antibodies (also called humanized antibodies), which contain the tumor-specific murine variable regions linked to a human immunoglobulin constant region. A chimeric recombinant version of L8A4 (chL8A4) was produced, which possesses the anti-EGFRvIII specificity of the murine L8A4 antibody together with the constant domains of human IgG$_2$ (for details of the generation of chL8A4 see Reist et al., 1997, and references therein). Human IgG$_2$ has a low affinity for $F_c$ receptors; the use of its constant regions thus minimizes non-specific uptake. After labeling with $^{125}$I- or $^{131}$I-SIPC, the tumor uptake properties of ch L8A4 were similar to those of murine L8A4. However, normal tissue uptake was increased by 2-fold at 72–120 hours (Reist et al., 1997), suggesting some differneces in processing and normal tissue uptake compared to the murine antibody. Further details on the production of chimeric antibodies by recombination methods can be found in Hoogenboom et al., 1996, U.S. Pat. No. 5,565,332.

Catabolism of Labeled mAbs

A number of groups have demonstrated that the catabolism of labeled mAbs and fragments is a complex process, resulting in the generation of multiple labeled catabolites (Garg et al., 1995; Rogers et al., 1996; Wu et al., 1997). With radioiodinated mAbs, an important consideration is the extent of dehalogenation which occurs in vivo, a phenomenon generally believed to be mediated by the enzymes normally involved in thyroid hormone metabolism. The liver, kidney, thyroid and other normal tissues possess multiple deiodinases of varying specificity for iodotyrosines and iodothyronines (Leonard and Rosenbert, 1977; Visser et al., 1988; Boye and Laurberg, 1984). Of potential relevance to the treatment of CNS tumors is the fact that thyroid hormone deiodinases also have been found in both human normal brain (Campos-Barros et al., 1996) and brain tumors (Mori et al., 1993). Proteases also can play a role in the degradation of labeled mAbs. The properties of the mAb constant region may influence its resistance to proteolysis and the nature of the catabolites that are generated. Accelerated proteolytic degradation of mAbs could occur in tumors due to the actions of the proteases involved in metastatic invasion (Liotta and Kohn, 1997). For example, cathepsin B is expressed in human gliomas at levels that appear to correlate with the degree of malignancy (Rempel et al., 1994; Mikkelsen et al., 1995; Sivaparvathi et al., 1995). This protease has a broad substrate specificity and has been shown to cleave peptide bonds in mAb conjugates (Li and Meares, 1993).

Internalization of mAbs creates an additional problem from a labeling perspective because it generally results in exposure of the labeled mAb to the numerous proteases found in lysosomes. Lysosomal degradation of a variety of mAbs labeled using conventional radioiodination methods has been characterized by the rapid release of radioiodine from the tumor cell in vitro, primarily as iodotyrosine (Geissler et al., 1991, 1992; Novak-Hofer et al., 1995; Press et al., 1996; Reist et al., 1996), and poor retention of radioactivity in tumor xenografts in vivo (van der Jagt et al., 1992; Reist et al., 1995; Sharkey et al., 1997a). The development of better methods for labeling internalizing mAbs requires an appreciation of the labeled catabolites created in the lysosomal compartment, and the ability of these labeled molecules to traverse the lysosomal membrane.

Nuclide Selection

Many ongoing clinical protocols involve administration of $^{131}$I-labeled mAbs directly into spontaneous cystic gliomas and surgically-created glioma resection cavities, and via the intrathecal route for neoplastic meningitis (Brown et al., 1996; Bigner et al., 1995, 1998). The presence of minimal residual disease makes these settings favorable for radioimmunotherapy (Sautter-Bihl et al., 1996) by minimizing the impact of non-uniformities in antigen expression, blood flow, permeability and interstitial pressure, as well as the binding site barrier, on tumor dose heterogeneity (Jain, 1996; Zhu et al., 1997). Because of their short range in tissue, the low-energy β-particles of $^{131}$I and the α-particles of $^{211}$At should be well-matched to therapeutic applications such as these which involve small tumor foci, thin sheets of compartmental tumor, and free-floating tumor cells. Although higher-energy β-emitters such as $^{90}$Y are attractive for other therapeutic applications, $^{131}$I should be more useful for treating micrometastases because it can deposit a higher fraction of its decay energy within the tumor (O'Donoghue et al., 1995; O'Donoghue, 1996; Nahum, 1996).

Initial diagnostic and therapeutic clinical trials with labeled mAbs were performed with $^{131}$I. Since then, methods have been developed for labeling mAbs with many other nuclides. Nevertheless, most clinical radioimmunotherapy trials still use $^{131}$I, and a strong rationale exists for continuing to do so. Even though its 364-keV γ ray is not ideal for imaging, it permits direct monitoring of the pharmacokinetics of an $^{131}$I-labeled mAb therapy dose, which provides valuable information concerning patient-specific dosimetry (Brown et al., 1996). Furthermore, better methods for imaging therapeutic levels of $^{131}$I in tumors are being developed (Smith et al., 1997a, 1997b). Other radioiodine nuclides are better suited for imaging. Particularly for quantitative applications, $^{123}$I is a more attractive nuclide for imaging mAbs via SPECT (Buchegger et al., 1995). SPECT imaging was performed following intravenous administration of $^{123}$I-labeled 81C6 to determine the effect of mAb protein dose on tumor-to-normal tissue ratios (Schold et al., 1993). Iodine-124 can be used for combining radioimmunoscintigraphy with PET (Arbit et al., 1995). The availability of multiple radioiodine nuclides emitting γ rays suitable for external detection is a major advantage not only for clinical applications but for preclinical studies as well. Paired-label experiments using $^{131}$I- and $^{125}$I-labeled mAbs (see Examples 24) can directly compare different labeling methods or mAbs in the same animals, and thereby factor out differences in antigen expression, tumor size, hemodynamics, and catabolic rate that can exist among groups of animals.

Astatine-211 generally has been considered to be the most promising α-emitter for radioimmunotherapy. In most settings, its 7.2-hr half life is more compatible with the pharmacokinetics of mAbs and mAb fragments than the alternative α-emitters $^{212}$Bi (61 min) and $^{213}$Bi (47 min). Each decay of $^{211}$At produces an α-particle of 5.87 to 7.45 MeV, with no accompanying β-emissions. A fortuitous consequence of the electron capture decay branch of $^{211}$At is the emission of 77–92-keV polonium K x-rays which are of sufficient energy to permit gamma counting and external-imaging of $^{211}$At distributions by planar methods and SPECT (Turkington et al., 1993; Johnson et al., 1995). A significant problem that has hindered the clinical investigation of $^{211}$At-labeled mAbs has been the reliable availability of sufficient activity levels of $^{211}$At. Using newly-developed internal cyclotron targets, more than 40 mCi/hr$^{211}$At can now be produced (Larsen et al., 1996; Schwarz et al., 1998), permitting the preparation of sufficient levels of $^{211}$At to permit clinical studies with $^{211}$At-labeled mAbs. The α-particles of $^{211}$At have a range of 55–70 μm in tissue, a characteristic that is well-matched to the treatment of compartmental-spread cancers including neoplastic meningitis, micrometastatic disease, and tumors in the circulation such as lymphomas.

Methods for Labeling mAbs with Radioiodine and $^{211}$At

Proteins labeled using direct iodination approaches frequently undergo rapid loss of label in vivo. Those methods primarily generate labeled tyrosine residues, resulting in the recognition of these iodotyrosines by the deiodinases normally involved in thyroid hormone metabolism. The chemical moieties of formula (II) can be used to circumvent this problem. For example, the reagent N-succinimidyl 3-iodobenzoate (SIB) can be synthesized in high yield via iododestannylation (Zalutsky and Narula, 1987). SIB exploits the rapid elimination of iodobenzoate catabolites from the body, reducing less uptake of radioactivity by normal tissues compared with iodide (Zalutsky and Narula, 1988). The related moiety N-succinimidyl 3-[$^{211}$At]astatobenzoate (SAB) can be prepared in a similar manner. When proteins are labeled with $^{211}$At using direct electrophilic substitution methods, rapid dehalogenation occurs, even under in vitro conditions (Aaij et al., 1975). Using SAB, it has been possible to label mAbs with retention of their tumor localizing capacity (Zalutsky et al., 1989b).

SIB and SAB can be used to directly radiohalogenate a ligand such as a mAb. While direct radiohalogenation using SIB or SAB decrease deiodination, they do not prevent loss of label from tumor cells after mAb internalization (Reist et al., 1996). The most widely investigated strategy for labeling internalizing mAbs attempts to exploit the resistance of certain oligosaccharides to degradation by lysosomal hydrolases (Thorpe et al., 1993). Preclinical evaluations have been reported with mAbs labeled using tyramine conjugates of cellobiose (TCB) (Ali et al., 1990; Reist et al., 1995), inulin (Thorpe et al., 1993) and dilactitol (Stein et al., 1995, 1997). Compared with other iodination methods, use of these conjugates for labeling internalizing mAbs generally increased the retention of radioiodine in tumor cells in vitro and in tumor xenografts in vivo. Unfortunately, the translation of these labeling methods into the clinical domain has been hindered by a number of problems, including mAb crosslinking and aggregation, compromised immunoreactivity, diminished specificity in tumor targeting, low conjugation efficiencies and specific activities, and increased retention in normal tissues such as liver, spleen, and kidneys (Pittman et al., 1983; Ali et al., 1990; Reist et al., 1995; Press et al., 1996; Stein et al., 1995, 1997).

An alternative strategy for labeling internalizing mAbs involves the coupling of a labeled prosthetic group to the mAb that is positively charged at lysosomal pH. Positively charged molecules such as Neutral Red and choroquine are avidly accumulated by lysosomes (Holtzman, 1989). Thus, if the labeled catabolites created during mAb proteolytic degradation are positively charged at lysosomal pH, then they also should be retained within the lysosome. In order to apply this strategy two positively charged chemical moieties, succinimidyl-iodo-pyridine carboxylate (SIPC) and succinimidyl-astato-pyridine carboxylate (SAPC), were developed (Garg et al., 1991, 1993). The use of SIPC for labeling mAb L8A4 resulted in significantly increased intracellular retention of radioactivity compared with other methods, with a concomitant decrease in radioactivity released from the cell (see Example 1). This verified that a positively charged radiohalogen label linked to an appropriate mAb has superior retention and resistance to degradation compared with labels that are not positively charged.

D-Amino-Acid Linkers

The proteolytic degradation of proteins in lysosomes results in rapid release of constituent L-amino acids from the cell (Reijngoud and Tager, 1977). This presumably accounts for the release of monoiodotyrosine from tumor cells following the internalization of mAbs that have been labeled by conventional methods (Geissler et al., 1991). D-amino acids are not natural substrates for endogenous enzymes (Milton et al., 1992), including those present in lysosomes (Ehrenreich and Cohn, 1969). This invention utilizes one or more D-amino acids in an oligopeptide linker between the mAb and the labeled prosthetic group, which enhances the trapping of radioactivity inside the tumor cell following mAb internalization.

The studies of Ehrenreich and Cohn (1969) offer some guidance as to the nature of the D-amino acid linker. Following endocytic uptake in lysosomes, a charged dipeptide and a neutral tripeptide were trapped, while 6 neutral dipeptides were not. Therefore, in order to maximize retention in lysosomes, the peptide linker should contain multiple positively charged amino acids, preferably coupled to positively charged SIPC or SAPC.

Schemes for preparing two preferred embodiments are shown in FIGS. 1A and 1B. In FIG. 1A, the N-terminal protected tetrapeptide α-N-Ac-D-Lys-D-Arg-D-Arg-D-Arg (SEQ ID NO: 1), which can be obtained from a custom synthesis laboratory is labeled by reaction with SIPC in the presence of triethylamine and DMF using conditions previously described (Garg et al., 1996; Vaidyanathan and Zalutsky, 1997). Arginine was selected for this purpose because its side chain is the most basic (pKa=13.2) of the naturally occurring amino acids. The labeled peptide is then coupled to the mAb using water-soluble 1-ethyl-3-(3-dimethylaminopropyl) carbodiimide (EDC) and sulfo N-hydroxysuccinimide in 4-morpholinoethanesulfonic acid buffer (MES), pH 4.5–5 (Staros et al., 1986; Gilles et al., 1990). The terminal amino group can be left in the protected form and should be cleaved in vivo.

An alternative procedure involves adding a D-Tyr to the N-terminal of the peptide and labeling the peptide directly using Iodogen (FIG. 1B). In this case, the N-terminal protected peptide might consist of, e.g., α-N-Ac-D-Tyr-D-Arg-D-Arg-D-Arg (SEQ ID NO:2). Monoiodo-D-tyrosine is more stable to deiodination in vivo than its L enantiomer (Kawai et al., 1990). This is probably related to stereospecific deiodinase recognition (Dumas et al., 1973). Nonetheless, SIPC and SIB are even more resistant to deiodination, rendering the D-Tyr peptide less useful despite its potential convenience.

The above disclosure generally describes the present invention. A more complete understanding can be obtained by reference to the following specific examples, which are provided herein for purposes of illustration only and are not intended to limit the scope of the invention.

EXAMPLE 1

Labeling mAbs using N-Succinimidyl 5-Halo-3-Pyridinecarboxylates

Preparation of SIPC. STPC is synthesized in 3 steps from 5-bromonicotinic acid as described (Garg et al., 1991) and used as the precursor for the preparation of SIPC and SAPC. Although published methods for labeling SIPC have been effective, they involve relatively high levels of tin precursor, a 60–65° C. reaction temperature, and HPLC purification. These features may be less than ideal for higher activity level preparations, particularly those intended for clinical use. Usisng a new procedure, radioiodination of SIPC can be accomplished at room temperature in greater than 80% yield using considerably less STPC. In this new procedure, 10 µg STPC in 10 µl CHCl$_3$ is added to a glass vial, and 2 µl of 1 N HCl, sodium [$^{131}$I]iodide, and 20 µl of N-chlorosuccinimide (2 mg/ml in CHCl$_3$) are added. The mixture is vortexed and reacted for 30 min. After addition of 100 µl of CHCl$_3$, [$^{131}$I]SIPC is purified by HPLC using a silica column eluted with hexane:ethyl acetate:AcOH (65:35:2).

Production of astatine-211. Astatine-211 can be produced on a cyclotron by bombarding natural bismuth metal targets with 28-MeV α-particles via the $^{209}$Bi(α,2n)$^{211}$At reaction. An internal target system specifically designed for $^{211}$At production has been described in detail in a recent publication (Larsen et al., 1996). Design features of this target that have permitted the production of high levels of $^{211}$At include a curved target face, small grazing angles, and electrically isolated graphite leading- and trailing-edge monitors for continuous beam current monitoring. It has been possible to use high cyclotron beam currents without excessive local heat deposition, which would cause loss of $^{211}$At from the target. Using this target, $^{211}$At production efficiency has been about 1 mCi per µA-hr, a level considerably higher than those obtained with an external target. Beam currents of 75 µA or more have been used routinely. A dry distillation procedure can be used to separate $^{211}$At from the cyclotron target, and the $^{211}$At can be trapped >50% yield in small volumes of NaOH, CHCl$_3$, or other solvents (Larsen et al., 1996). Using this method, $^{211}$At can be produced at levels that are sufficient to permit the clinical use of $^{211}$At-labeled radiopharmaceuticals.

Preparation of SAPC This procedure was described in a recent publication (Foulon et al., 1998). 20 µl of 0.01 N NaOH is added to a vial containing the $^{211}$At activity (1 mCi in 50 µl CHCl$_3$), and after vortexing gently, the organic layer is evaporated under a stream of nitrogen. The activity is transferred to a second vial and the pH of the solution adjusted to <5 by the addition of acetic acid:chloroform, 5:95. N-chlorosuccinimide (10 µl, 13.3 mg/ml in CHCl$_3$) and STPC (500 µg in 10 µl CHCl$_3$) are added and the reaction allowed to proceed at 65° C. for 5 min. SAPC is purified by HPLC using the same system as described for SIPC. Yields for SAPC have been variable. Important factors to optimize include levels of tin precursor, reaction time and temperature, oxidant, and solvent. The latter variable appears to be particularly important; SAPC was obtained in 70% yield when labeling was performed in a mixture of dichloromethane and THF.

Coupling SIPC and SAPC to mAbs. The organic solvent is evaporated from the HPLC fractions containing SIPC or SAPC, and the residue is transferred to a small glass vial and evaporated to dryness with a stream of nitrogen. The mAb in pH 8.5 borate buffer is added, and the mixture is incubated on a rotary shaker for 15 min. The reaction is terminated by the addition of 0.3 ml 0.2 M glycine. The labeled mAb is purified using a 1×10-cm Sephadex G-25 column. At MAb concentrations of 3 mg/ml, coupling efficiencies of 70% are obtained routinely.

EXAMPLE 2

Evaluation of mAb after Labeling

HPLC. An aliquot of labeled mAb is analyzed by size-exclusion HPLC on a TSK3000 column to determine the percentage of radioactivity present as aggregates, monomeric IgG and low molecular weight impurities.

Immunoreactive fraction For anti-EGFRvIII mAbs, homogenates of EGFRvIII-positive tumor xenograft (U87MGΔEGFR or HC2 20 d2) and EGFRvIII-negative normal rat brain are stored at −135° C. until needed. About 5 ng of labeled mAb is incubated overnight at 4° C. in triplicate with 100, 300, and 500 mg of each homogenate, and then washed 3 times with ice-cold 1% bovine serum albumin (BSA) in phosphate buffered saline (PBS). Immunoreactive fractions are calculated according to the method of Lindmo et al. (1984).

Affinity constant. Scatchard analysis is used to measure both the binding affinity of mAbs after labeling and the average number of receptors/cell. At least 10 serial dilutions of labeled mAb (10 ng/ml to 10 µg/ml) are incubated at 4° C. overnight in quadruplicate with 1×10$^6$ EGFRvIII-expressing U87MGΔEGFR cells or NIH 3T3 receptor-negative control cells. Cells are pelleted, washed three times with 1% BSA/PBS, and cell-associated activity is counted in an automated gamma counter. Data are analyzed using the RADLIG radioligand binding program (Biosoft, Ferguson, Mo.).

Internalization and cellular processing. Radiolabeled mAbs are incubated with U87MGΔEGFR cells in antibody excess (3 mg/10$^6$ cells) for 1 hr at 4° C., and unbound mAb is removed by washing with 1% BSA/PBS. The temperature is adjusted to 37° C., and aliquots are removed for analysis after 0, 1, 2, 4, 8, and 20 hr. Cells are pelleted, and the culture supernatant saved for counting. Cells are washed twice with Zinc Option media (pH 2) to determine surface-bound activity. Protein-associated activity in the culture supernatant is determined by precipitation with 12.5% TCA, or for experiments involving $^{211}$At, methanol. Cell-internalized, cell-surface, supernatant protein-associated, and supernatant non-protein associated activity are plotted as a function of time (Reist et al., 1995). 25 mM choroquine can be included in the incubation medium to study the effect of inhibiting lysosomal function on the cellular processing of labeled anti-EGFRvIII mAbs (Press et al., 1990).

EXAMPLE 3

Evaluation of Cytotoxicity In Vitro

The cytotoxicity of internalized mAbs labeled with β- and α-emitters can be evaluated in vitro. Dosimetry calculations suggest that the cytotoxicity of Auger electrons, α-particles and β-particles emitted from intracellular sites of decay are higher than for those occurring on the cell membrane, and in vitro experimental data obtained with an $^{125}$I-labeled mAb are consistent with this prediction (Goddu et al., 1994; Daghighian et al., 1996). The cytotoxicity of labeled mAbs and other compounds for tumor cells has been investigated under single-cell conditions (Strickland et al., 1994), as microcolonies (Larsen et al., 1998) and in spheroids (Hauck et al., 1998).

The proliferative capacity of EGFRvIII-positive cells can be determined using a limiting dilution clonogenic assay. Using this assay format, the cytotoxicity of m-[$^{211}$At]astatobenzylguanidine was assessed down to a survival fraction of about 10$^{-5}$ (Strickland et al., 1994). The preferred cell line is U87MGΔEGFR, because it is currently the primary line utilized for the generation of EGFRvIII-positive xenografts in vivo. However, other EGFRvIII-expressing lines such as HC2 20 d2, NR6M and D1105 can also be studied because they differ with regard to the rate and extent to which they internalize anti-EGFRvIII mAbs (Reist et al., 1997). In this assay, cells in exponential growth are mechanically harvested, counted in a hemocytometer, and incubated with varying activity concentrations of labeled mAb for 30 min on a rotating shaker at 37° C. A cell density of about 1×10$^6$ cells/ml is used to minimize nonspecific killing from unbound activity in the medium. As a nonspecific control, incubations are performed in which at least a 100-fold excess of unlabeled mAb have been added to the cells. Following incubation, cells are centrifuged at 100 g for 10 min and the supernatant is aspirated. The cell pellet is resuspended, the wash procedure is repeated, and the cells are resuspended at a concentration of 10$^6$ cells/ml in Zinc Option minimal essential medium supplemented with 15% fetal calf serum. The cells are then passed through 9 fivefold serial dilutions resulting in final cell concentrations ranging from 10$^5$ to 0.256 cells plated per well. A total of six replicate wells for each cell concentration are made in low-evaporation, tissue-culture treated, polystyrene 96-well plates. After a 12-day incubation at 37° C. in a humidified incubator, the wells of each plate are scored as either growth positive or growth negative based on the presence or absence of at least one clonal colony of 30 or more cells. The mean of the dose response function for each therapy and the estimated number of clonogenic units per ml are calculated using a Spearman estimate (Johnson and Brown, 1961). The clonogenic response of each treatment group, expressed as a percentage of two untreated controls, is then plotted against the mean activity added per ml. In parallel, the uptake and retention of radioactivity by the target cells in both the cell-surface and intracellular compartments are measured to permit calculation of dosimetry, and to study the potential effect of internalization on cytotoxicity. The sites of intracellular localization are documented by immunofluorescence microscopy (Reist et al., 1995).

EXAMPLE 4

Evaluation of Therapeutic Efficacy in Xenograft Models

Prior to initiation of therapy studies in tumor-bearing animals, the maximum tolerated dose (MTD) and $LD_{10}$ (dose lethal to 10% of animals) are determined. Normal athymic mice or rats are given either saline or half-log increments of labeled mAb and then followed for weight loss, neurological symptoms and death. The mean weight is monitored daily and the animals are autopsied within 12 hr of death to look for histological evidence of normal organ toxicity. Radiotherapy studies in tumor-bearing animals are performed at 80% of the MTD.

Subcutaneous xenografts These studies can be performed using protocols described previously (Schuster et al., 1991). Mice with progressively growing U87MGΔEGFR subcutaneous xenografts are randomly assigned into groups of 10 animals when tumors have reached 150–200 mm$^3$. Groups of 10 animals are administered either saline, unlabeled L8A4, or two activity levels of labeled L8A4 and P3X63Ag8 nonspecific control mAb. Response is evaluated in terms of growth delay and tumor regression. Growth delay is defined as the difference in days between when the treatment and control groups reach 1000, 2000, 3000, 4000 and 5000 mm. Tumor regression is defined as two consecutive volume measurements less than the tumor volume on the day of treatment. Statistical significance is determined using the Wilcoxon rank sum test. For radiation absorbed dose calculations, tissue distributions are measured in parallel groups of 5 animals receiving therapeutic doses of labeled mAbs. These studies are necessary because trace-level mAb distribution studies can underestimate radiation dose received by tumor due to rapid xenograft growth (Lee et al., 1988). Based on the results of single-dose trials, multi-dose therapeutic regimens can be investigated as described (Colapinto et al., 1990).

Intracranial xenografts. The protocol followed is similar to that reported previously (Colapinto et al., 1990). On the day prior to treatment, the animals are randomized according to body weight, and 10 mice are used per treatment group. Five additional mice are killed on the day of treatment to confirm the existence of tumors and to determine the average tumor volume present at the initiation of therapy. Experiments are begun when tumor size is 15–20 mm$^3$. The animals are kept in individual cages in a lead-shielded room and are checked twice a day for survival. Animals are examined at death to confirm the presence of an intracranial tumor. Therapeutic response is evaluated as survival prolongation using the product-limit estimator of Kaplan and Meier (1958).

Neoplastic meningitis. These studies can be performed in an athymic rat model of neoplastic meningitis using protocols similar to those described in a recent publication (Zalutsky et al., 1994). Subarachnoid catheters are placed in female, BIG:NIMR-rnu[SPF] athymic rats weighing 200–250 mg (Fuchs et al., 1990). Animals are anesthetized with ketamine/xylazine and placed in a stereotactic frame. A midline sagittal incision is made from the inion to the laminal arch of C1, the atlanto-occipital membrane is exposed, and the outer membrane and underlying cisterna magna dura are opened under magnification using an operating microscope. A PE-10 catheter is inserted into the subarachnoid space and passed along the posterior aspect of the spinal cord to the lumbar region. After the catheter is fixed in place with dental epoxy, it is passed through the skin lateral to the incision and the wound is closed. Animals are allowed to recover and only those exhibiting normal motor and sensory function are used. Neoplastic meningitis is induced by injecting 5×10$^6$ U87MGΔEGFR cells in 40 µl through the catheter with a Hamilton syringe and therapy studies are initiated 5–8 days later. Groups of 10 animals receive either graded doses of labeled mAbs or controls. Therapeutic response is assessed as survival prolongation using the product-limit estimator of Kaplan and Meier (1958). After death, the spinal column and skull are removed intact and processed for histology as described (Zalutsky et al., 1994).

EXAMPLE 5

Quantitative Autoradiography and Radiation Dosimetry

Quantitative Autoradiography (QAR). QAR is used to assess the regional distribution of radioactivity within tumor and adjacent normal tissue. We have used QAR to study the heterogeneity of murine 81C6 delivery in intracranial and subcutaneous D-54 MG xenografts (Blasberg et al., 1987), as well as to investigate the effects of tumor-localized hyperthermia on the homogeneity of mAb deposition in subcutaneous xenografts (Zalutsky et al., 1996). QAR is performed in single-label format with animals receiving either $^{125}$I- or $^{211}$At-labeled mAb. At time intervals selected based on the tissue distribution studies, animals are killed and tumors are removed and snap-frozen in liquid nitrogen. Tumors are mounted on planchettes in M-1 mounting medium and 20 µm sections are step cut on a cryonicrotome at −20° C. Sections are placed on glass slides, dried on a slide warmer at 65° C. and placed in film cassettes for an exposure period appropriate for the activity level in the section. After developing the film, the sections are stained with hematoxylin and eosin, and a digital image is generated for alignment with the autoradiographic image. The activity concentration in the autoradiograph regions is quantified by comparison with standards which are prepared by adding known amounts of $^{125}$I or $^{211}$At to rat brain homogenate which is frozen and treated identically to the tumor samples. Image analysis can be performed using an Amersham RAS R-1000 system and the in situ grain image analysis program obtained from Loats Associates. Depending on the spacial resolution required, image analysis can also be performed using a Storm 860 Phosphoimager.

Radiation Absorbed Dose Calculations. A modified MIRD approach can be used in which a uniform distribution of radioactivity in tumor is assumed. As suggested in a recent review of β-particle dosimetry in experimental tumors (Leichner and Kwok, 1993), the effect of β-particle absorbed fraction, particularly in smaller tumors, and heterogeneous source distribution within the tumor, which can be assessed by QAR, should be considered. Calculations for $^{211}$At-labeled mAbs can be done as described (Zalutsky et al., 1997). However, because of the stochastic fluctuation of dose in small target volumes, a realistic assessment of $^{211}$At radiation absorbed dose requires microdosimetric-level calculations (Humm et al., 1993). A method for calculating the small-scale dosimetry of $^{211}$At using chord-length distributions obtained from digitized histological images has recently been described (Akabani and Zalutsky, 1997).

EXAMPLE 6

Internalization and Retention of Mab L8A4 Labeled with $^{125}$I or $^{131}$I Using SIPC SIPC was labeled with $^{125}$I or $^{131}$I via iododestannylation of STPC using N-chlorosuccinimide as the oxidant (Garg et al., 1991). After a 5-min reaction at 60–65° C. and HPLC purification, the product was obtained in 60–80% yield. The efficiency for labeling mAb L8A4 by reaction with SIPC was 52–71% (Reist et al., 1996), values nearly twice those obtained for the conjugation of TCB to this mAb Reist et al., 1995). No evidence of protein aggregation was observed by size-exclusion HPLC for L8A4 labeled using SIPC, while 10–20% of the radioiodine was present as aggregates in most of the TCB preparations. Immunoreactive fractions for L8A4 labeled using SIPC were higher than those obtained when this mAb was labeled using either Iodogen or TCB. In vitro assays were performed to compare the internalization and cellular processing of L8A4 labeled using Iodogen, SIPC and SIB (a reagent which like SIPC, minimizes mAb deiodination, but unlike SIPC, is not positively charged). Use of SIPC for labeling L8A4 resulted in significantly increased intracellular retention of radioactivity compared with other methods, with a concomitant decrease in supernatant counts. For example, after a 4 hr incubation at 37° C., the intracellular compartment had 24.0±0.9% of the activity for mAb labeled using SIPC compared with 13.2±0.5% with SIB, while 12.2±0.3% (SIPC) and 36.1±1.6% (SIB) of the activity was found in the cell culture supernatant (FIG. 2). The results suggest that the enhanced cellular retention for mAb labeled using SIPC is not related to decreased deiodination.

EXAMPLE 7

Internalization, Retention, and Tissue Distribution of L8A4 Labeled with $^{211}$At Using SAPC N-succinimidyl 5-[$^{211}$At]astato-3-pyridinecarboxylate (SAPC) was synthesized from STPC using N-chlorosuccinimide as the oxidant. The efficiency for labeling L8A4 with SAPC was identical to that observed with SIPC. For $^{211}$At-labeled L8A4, immunoreactive fractions were 69–89% and the affinity ($K_A$) for binding to the U87MGΔEGFR cell line was (9.7±1.3)×10$^8$ M$^{-1}$. Internalization and processing assays were performed as described for radioiodinated mAbs except that protein-associated activity for $^{211}$At was measured using methanol rather than TCA precipitation because we found that 98% of free [$^{211}$At]astatide was precipitated in the TCA assay. Comparable levels of intracellular counts were seen for $^{211}$At- and $^{131}$I-labeled L8A4 at early time points, but there were higher levels of methanol-soluble cell culture supernatant activity for $^{211}$At, suggesting a more rapid release of $^{211}$At-labeled catabolites. The tissue distribution of $^{211}$At- and $^{131}$I-labeled L8A4 was evaluated in athymic mice bearing subcutaneous U87MGΔEGFR xenografts. Both nuclides maintained constant tumor levels over the 6 to 24 hr experimental period, with slightly higher uptake observed for $^{211}$At ($^{211}$At, 21.6±2.7% ID/g; $^{131}$I, 18.7±2.4% ID/g at 12 hr). Levels of $^{211}$At were somewhat higher than $^{131}$I in spleen, lungs and stomach, tissues known to accumulate [$^{211}$At]astatide (Garg et al., 1990).

EXAMPLE 8

In Vitro Binding and Internalization of mAbs Labeled With a Positively Charged D-Amino Acid Linker A paired-label in vitro assay was performed to compare the internalization and cellular processing of mAb L8A4 labeled with $^{131}$I using Iodogen and $^{125}$I using the oligopeptide linker method of this invention. Monoclonal antibody L8A4 was labeled using the oligopeptide linker as follows. The peptide α-N-Ac-D-Lys-D-Arg-D-Tyr-D-Arg-D-Arg (KRYRR) (SEQ ID NO:3) was obtained from a custom synthesis laboratory and labeled with $^{125}$I using the Iodogen method. Reverse phase HPLC was used to isolate $^{125}$I-labeled KRYRR (SEQ ID NO:3) in >97% yield, and the labeled peptide was activated by reaction with sulfo-SMCC at room temperature for 30 min. Murine anti-EGFRvIII mAb L8A4 was reacted with 2-imino thiolane to generate free thiol groups and then reacted with activated $^{125}$I-labeled peptide-L8A4. The conjugate was isolated over a Sephadex G-25-PD10 column. The yield was about 35%.

The EGFRvIII-expressing U87MGΔEGFR cell line was used, and the results are shown in FIG. 3. Internalized and total cell-associated counts were significantly higher with the oligopeptide labeling method at the three time points examined; the differences between the two labeling methods increased with time. For example, after a 24 hr incubation at 37° C., the percentage of activity retained as internalized counts was nearly four times higher with the oligopeptide (Iodogen, 5.0±1.2%; oligopeptide, 18.8±5.4%). Likewise, the total cell-associated (internalized+cell surface) activity was 5.3 times higher for $^{125}$I-labeled oligopeptide-L8A4 at this time (Iodogen, 11.1±1.0%; peptide, 58.3±12.4%). In comparison, when the peptide used by Govindan et al. (1998) and Stein et al. (1998) was used to label an internalizing mAb, a two- to three-fold increase in cell-associated activity was observed compared with directly labeled mAb.

EXAMPLE 9

Tumor Uptake of mAbs mAbs Labeled With a Positively Charged D-Amino Acid Linker

The tissue distribution of murine L8A4 labeled with $^{125}$I using the oligopeptide method and with $^{131}$I using Iodogen were directly compared in athymic mice bearing subcutaneous EGFRvIII-expressing, U87MGΔEGFR human glioma xenografts. Monoclonal antibody L8A4 was labeled as described in Example 8. The tumor uptake of the two labeled mAbs is shown in FIG. 4. Significantly higher tumor levels were observed at all time points. The peptide labeling method increased the tumor retention of radioiodine activity by 194±38% at 12 hr, 296±47% at 24 hr, 468±91% at 36 hr, 542±68% at 48 hr, and 547±69% at 72 hr. In comparison, the peptide described by Govindan et al. (1998) and Stein et al. (1998) increased tumor uptake by only 170% at 24 hr and 270% at 72 hr. In addition, the tumor delivery advantage achieved with the oligopeptide method was considerably greater than that observed in previous studies with murine L8A4 labeling using other methods (TCB and SIPC) developed for the radiodination of internalizing mAbs (Reist et al., 1995, 1996, 1997).

EXAMPLE 10

Thyroid Uptake of Radioactivity Released from mAbs Labeled With a Positively Charged D-Amino Acid Linker Thyroid accumulation is generally used as an indicator of dehalogenation of radioiodinated compounds in vitro. As shown in FIG. 5, thyroid levels for L8A4 labeled using the oligopeptide method of this invention (as described in Example 8) were 52±9%, 29±5%, 17±1%, 11±1%, and 11±2% of those for mAb labeled using Iodogen at 12, 24, 36, 48, and 72 hr, respectively.

EXAMPLE 11

Tumor-to-Blood Uptake Ratio of Radioactivity From mAbs Labeled With a Positively Charged D-Amino Acid Linker With previous labeling techniques, tumor-to-blood label uptake ratios never were greater than 1 with murine L8A4 labeled using Iodogen (Reist et al., 1995). In contrast, tumor-to-blood ratios for mAb labeled using the oligopeptide method of this invention (as described in Example 8) increased from 1.8±0.6 at 12 hr to 7.2±1.0 at 72 hr (FIG. 6). These ratios were significantly higher than those obtained with other labeling methods developed for use with internalizing mAbs (Reist et al., 1995, 1996, 1997).

REFERENCES

Aaij, C., Tschroots, W. R. J. M., Lindner, L. and Feltkamp, T. E. W. (1975) The preparation of astatine labelled proteins. Int. J. Appl. Radiat. Isot. 26:25–30.

Akabani, G. and Zalutsky, M. R. (1997) Microdosimetry of astatine-211 using histological images: application to bone marrow. Radiat. Res. 148:599–607.

Ali, S. A., Warren, S. D., Richter, K. Y., Badger, C. C., Eary, J. F., Press, O. W., Krohn, K. A., Bernstein, I. D., and Nelp, W. B. (1990) Improving the tumor retention of radioiodinated antibody: aryl carbohydrate adducts. Cancer Res. 50:783s–788s.

Arbit, E., Cheung, N. K., Yeh, S. D., Daghighian, F., Zhang, J. J., Cordon-Cardo, C., Pentlow, K., Canete, A., Finn, R, and Larson, S. M. (1995) Quantitative studies of monoclonal antibody targeting to disialoganglioside GD2 in human brain tumors. Eur. J. Nucl. Med 22:419–425.

Baselga, J. and Mendelsohn, J. (1994) Receptor blockade with monoclonal antibodies as anti-cancer therapy. Pharmaol Ther. 64:127–154.

Bast Jr. R. C., Zalutsky, M. R., and Frankel, A. (1997) Monoclonal Serotherapy. In: Holland, J. F., Frei, E. III., Bast, R. C., Jr., Kufe, D. W., Morton, D. L., and Weichselbaum, R. R., eds. Cancer Medicine $4^{th}$ Edition. Baltimore: Williams and Wilkins, p. 1245–1262.

Bigner, D. D., Brown, M., Coleman, R. E., Friedman, A. H., Friedman, H. S., McLendon, R. E., Bigner, S. H., Wikstrand, C. J., Pegram, C. N., Kerby, T., and Zalutsky, M. R. (1995) Phase I studies of treatment of malignant gliomas and neoplastic meningitis with $^{131}$I-radiolabeled monoclonal antibodies anti-tenascin 81C6 and anti-chondroitin proteoglycan sulfate Me1-14 F(ab')$_2$—A preliminary report. J. Neuro-Oncol. 24:109–122.

Bigner, D. D., Brown, M. T., Friedman, A. H., Coleman, R. E., Akabani, G., Friedman, H. S., Thorstad, W. L., McLendon, R. E., Bigner, S. H., Zhao, X.-G., Pegram, C. N., Wikstrand, C. J., Herndon II, J. E., Vick, N. A., Paleologos, N., Cokgor, I., and Zalutsky, M. R. Iodine-131-labeled anti-tenascin monoclonal antibody 81C6 treatment of patients with recurrent malignant gliomas: Phase I trial results. (submitted, 1998).

Blasberg, R. G., Nakagawa, H., Bourdon, M. A., Groothuis, D. R., Patlak, C. S., and Bigner, D. D. (1987) Regional localization of a glioma-associated antigen defined by monoclonal antibody 81C6 in vivo: kinetics and implications for diagnosis and therapy. Cancer Res. 47:4432–4443.

Boye; N. and Laurberg, P. (1984) Deiodination of $T_4$ to $T_3$ and $rT_3$ by microsomes from normal human thyroid tissue. Mol. Cell Endocrinol. 37:295–299.

Bradwell, et al. (1985) In Monoclonal Antibodies for Cancer Detection and Therapy. Baldwin et al., Eds., pp. 65–85, Academic Press.

Brady, L. W., Miyamoto, C., Woo, D. V., Rackover, M., Emrich, J., Bender, H., Dadparvar, S., Steplewski, Z., Koprowski, H., Black, T., Lazzaro, B., Nair, S., McCormack, T., Nieves, J., Morabito, M., and Eshleman, J. (1992) Malignant astrocytomas treated with iodine-1 25 labeled monoclonal antibody 425 against epidermal growth factor receptor: a phase II trial. Int. J. Radiat. Oncol. Biol. Phys. 22:225–230.

Britton, K. E. and Granowska, M. (1996) Immunoscintigraphy—importance for researchers and patients. Acta Oncologica 35:313–317.

Brown, M. T., Coleman, R. E., Friedman, A. H., Friedman, H. S., McLendon, R. E., Reiman, R., Felsberg, G. J., Tien, R. D., Bigner, S. H., Zalutsky, M. R., Zhao, X. G., Wikstrand, C. J., Pegram, C. N., Herndon II, J. E., Vick, N. A., Paleologos, N., Fredericks, R. K., Schold, Jr., S. C., and Bigner, D. D. (1996) Intrathecal $^{131}$I-labeled anti-tenascin monoclonal antibody 81C6 treatment of patients with leptomeningeal neoplasms or primary brain tumor resection cavities with subarachnoid communication: Phase I trial results. Clin. Cancer Res. 2:963–972.

Buchegger, F., Mach, J. -P., Pelegrin, A., Gillet, M., Vogel, C. A., Buclin, T., Ryser, J. E., Delaloye, B., and Delaloye, A. B. (1995) Radiolabeled chimeric anti-CEA antibody compared with the original mouse monoclonal antibody for surgically treated colorectal carcinoma. J. Nucl. Med 36:420–429.

Campos-Barros, A., Hoell, T., Musa, A., Sampaolo, S., Stoltenburg, G., Pinna, G., Eravci, M., Meinhold, H., and Baumgartner, A. (1996) Phenolic and tyrosyl ring iodothyronine deiodination and thyroid hormone concentrations in the human central nervous system. J. Clin. Endocrinol. Metab. 81:21792185.

Colapinto, E. V., Zalutsky, M. R., Archer, G. E., Noska, M. A., Friedman, H. S., and Bigner, D. D. (1990) Radioimmunotherapy of intracerebral human glioma xenografts with $^{131}$I-labeled F(ab')$_2$ fragments of monoclonal antibody Mel-14. Cancer Res. 50:1822–1827.

Daghighian, F., Barendswaard, E., Welt, S., Humm, J., Scott, A., Willingham, M. C., McGuffie, E., Old, L. J., and Larson, S. M. (1996) Enhancement of radiation dose to the nucleus by vesicular internalization of iodine-125-labeled A33 monoclonal antibody. J. Nucl. Med. 37:1052–1057.

De Santes, K., Slamon, D., Anderson, S. K., Shepard, M., Fendly, B., Maneval, D., and Press, O. (1992) Radiolabeled antibody targeting of the HER-2/neu oncoprotein. *Cancer Res.* 52:1916–1923.

Dumas, P., Maziere, B., Autissier, N., and Michel, R. (1973) Specificity of thyroidal and hepatic microsomal iodotyrosine deiodinase. *Biochem. Biophys. Acta* 293:36–47.

Ehrenreich, B. A. and Cohn, Z. A. (1969) The fate of peptides pinocytosed by macrophages in vitro. *J. Exp. Med* 129:227–243.

Foulon, C. F., Alston, K. L. and Zalutsky, M. R. (1998) Astatine-211 labeled biotin conjugates resistant to biotinidase for use in pretargeted radioimmunotherapy. *Nucl. Med Bio.* 25:81–88.

Fraker, P. J., and Speck Jr., J. C. (1978) Protein and cell membrane iodinations with a sparingly soluble chloramide, 1,3,4,6-tetrachloro-3α,6α-diphrenylglycoluril. *Biochem. Biophys. Res. Commun.* 80:849–857.

Fuchs, H. E., Archer, G. E., Colvin, O. M., Bigner, S. H., Schuster, J. M., Fuller, G. N., Muhlbaier, L. H., Schold, S. C. Jr., Friedman, H. S., and Bigner, D. D. (1990) Activity of intrathecal 4-hydroperoxycyclophosphamide in a nude rat model of human neoplastic meningitis. *Cancer Res.* 50:1954–1959.

Garcia de Palazzo, I., Adams, G. P., Sundareshan, P., Wong, A. J., Testa, J. R., Bigner, D. D., and Weiner, L. M. (1993) Expression of mutated epidermal growth factor receptor by non-small cell lung carcinomas. *Cancer Res.* 53:3217–3220.

Garg, P. K., Harrison, C. L., and Zalutsky, M. R. (1990) Comparative tissue distribution of the alpha emitter $^{211}$At and $^{131}$I as labels of a monoclonal antibody and F(ab')$_2$ fragment. *Cancer Res.* 50:3514–3520.

Garg, S., Garg, P. K. and Zalutsky, M. R. (1991) N-succinimidyl-5(trialkylstannyl)-3-pyridine carboxylates: a new class of reagents for protein radioiodination. *Bioconjugate Chem.* 2:50–56.

Garg, S., Garg., P. K., Zhao, X- G., Friedman, H. S., Bigner, D. D., and Zalutsky, M. R. (1993) Radioiodination of a monoclonal antibody using N-succinmimidyl-5-iodo-3-pyridinecarboxylate. *Nucl Med Biol.* 20:835–842.

Garg, P. K., Alston, K. L., and Zalutsky, M. R. (1995) Catabolism of radioiodinated murine monoclonal antibody F(ab')$_2$ fragment labeled using N-succinimidyl 3-iodobenzoate and iodogen methods. *Bioconjugate Chem.* 6:493–501.

Garg, P. K., Alston, K. L., Welsh, P. C., and Zalutsky, M. R. (1996) Enhanced binding and inertness to dehalogenation of α-melanotropic peptides labeled using N-succinimidyl 3-iodobenzoate. *Bioconjugate Chem.* 7:233–239.

Geissler, F., Anderson, S. K., and Press, O. (1991) Intracellular catabolism of radiolabeled anti-CD3 antibodies by leukemic T cells. *Cell Immunol.* 137: 96–110.

Gilles, M. A., Hudson, A. Q., and Borders Jr., C. I. (1990) Stability of water-soluble carbodiimides in aqueous solution. *Anal. Biochem.* 184:244–248.

Goddu, S. M., Rao, D. V., and Howell, R. W. (1994) Multicellular dosimetry for micrometastases: dependence of self-dose versus cross-dose to cell nuclei on type and energy of radiation and subcellular distribution of radionuclides. *J Nucl. Med* 35:521–530.

Govindan, S. V., Goldenberg, D. M., Stein, R., Mattes, M. J., Shih, L. B., McBride, W. J., Hansen, H. J., and Griffiths, G. L. (1998) Peptide-Based Residualizing Radioiodine Labels for Radioimmunotherapy. *J. Nuclear Med* 39:223P.

Hansen, H. J., Ong, G. L., Diril, H., Valdez, A., Roche, P. A., Griffiths, G. L., Goldenberg, D. M., and Mattes, M. J. (1996) Internalization and catabolism of radiolabeled antibodies to the MHC class-II invariant chain by B-cell lymphomas. *Biochem J* 320:293–300.

Hauck, M. L., Larsen, R. H., Welsh, P. C., and Zalutsky, M. R. (1998) Cytotoxicity of α-particle-emitting astatine-211-labelled antibody in tumour spheroids: no effect of hyperthermia. *Br. J. Cancer* 77:753–759.

Holtzman, E. (1989) Lysosomes, pp. 95–100. Plenum Press, N. Y. Hoogenboom, H. R. J. M., Baier, M., Jespers, L. S. A. T., and Winter, G. P. (1996) Production of chimeric antibodies—a combinatorial approach. U.S. Pat. No. 5,565,332, assigned to Medical Research Council, London and Cambridge Antibody Technology, Melbourn, England.

Humm, J. L., Roeske, J. C., Fisher, D. R., and Chen, G. T. Y. (1993) Microdosimetric concepts in radioimmunotherapy. *Med. Phys.* 20:535–541.

Humphrey, P. A., Wong, A. J., Vogelstein, B., Zalutsky, M. R., Fuller, G. N., Archer, G. E., Freidman, H. S., Kwatra, M. M., Bigner, S. H., and Bigner, D. D. (1990). Antisynthetic peptide antibody reacting at the fusion junction of deletion-mutant epidermal growth factor receptors in human glioblastoma. *Proc. Natl. Acad. Sci. USA* 87:4207–4211.

Jain, R. K. (1996) Delivery of molecular medicine to solid tumors. *Science* 271:1079–1080.

Johnson, E. A., and Brown, B, W., Jr. (1961) The Spearman estimator for serial dilution assays. *Biometrics* 17:79–88.

Johnson, E. L., Turkington, T. G., Jaszczak, R. J., Vaidyanathan, G., Green, K. L., Coleman, R. E., and Zalutsky, M. R. (1995) Quantitation of $^{211}$At in small volumes for evaluation of targeted radiotherapy in animal models. *Nucl. Med. Biol.* 22: 45–54.

Kairemo K. J. A. (1996) Radioimmunotherapy of solid cancers. *Acta Oncologica* 35:345–355.

Kaminski, M. S., Zasadny, K. R., Francis, I. R., Fenner, M. C., Ross, C. W., Milik, A. W., Estes, J., Tuck, M., Regan, D., Fisher, S., Glenn, S. D., and Wahl, R. L. (1996) Iodine-131-anti-B1 radioimmunotherapy for B-cell lymphoma. *J. Clin. Oncol.* 14:1974–1981.

Kaplan, E. L. and Meier, P. (1958) Nonparametric estimation from incomplete observations. *J. Amer. Statist. Assoc.* 53:457–481.

Kawai, K., Fujibayashi, Y., Saji, H., Konishi, J., Kubodera, A., and Yokoyama, A. (1990) Monoiodo-D-tyrosine, an artificial amino acid radiopharmaceutical for selective measurement of membrane amino acid transport in the pancreas. *Nucl. Med Biol.* 17:369–376.

Larsen, R. H., Wieland, B. W., and Zalutsky, M. R. (1996) Evaluation of an internal cyclotron target for the production of astatine-211 via the $^{209}$Bi(α,2n)$^{211}$At reaction. *Appl. Radiat. Isotop.* 47:135–143.

Larsen, R. H., Akabani, G., Welsh, P., and Zalutsky, M. R. (1998) The cytotoxicity and microdosimetry of $^{211}$At-labeled chimeric monoclonal antibodies on human glioma and melanoma cells in vitro. *Radiat. Res.,* 149:155–162.

Larson, S. M. (1995) Improving the balance between treatment and diagnosis: a role for radioimmunodetection. *Cancer Res. (Suppl.)* 55:5756s–5758s.

Laske, D. W., Youle, R. J., and Oldfield, E. H. (1997) Tumor regression with regional distribution of the targeted toxin TF-CRM107 in patients with malignant brain tumors. *Nature Medicine* 3:1362–1368.

Lee, Y.-S., Bullard, D. E., Zalutsky, M. R., Coleman, R. E., Friedman, H. S., Colapinto, E. V., and Bigner, D. D. (1988) Therapeutic efficacy of antiglioma mesenchymal extracellular matrix $^{131}$I radiolabeled murine monoclonal antibody in a human glioma xenograft model. *Cancer Res.* 48:559–566.

Leichner, P. K. and Kwok, C. S. (1993) Tumor dosimetry in radioimunotherapy: methods of calculation for beta particles. *Med Phys.* 20:529–534.

Leonard, J. L. and Rosenbert, I. N. (1977) Subcellular distribution of thyroxine 5'-deiodinase in the rat kidney: a plasma membrane location. *Endocrinology* 103:274–280.

Li, M. and Meares, C. F. (1993) Synthesis, metal chelate stability studies, and enzyme digestion of a peptide-linked DOTA derivative and its corresponding radiolabeled immunoconjugates. *Bioconjugate Chem.* 4:275–283.

Lindmo, T., Boven, E., Cuttitta, F., Fedoroko, J. and Bunn, P. A. Jr. (1984) Determination of the immunoreactive fraction of radiolabeled monoclonal antibodies by linear extrapolation to binding at infinite antigen excess. *J. Immunol. Methods* 72:77–89.

Liotta, L. A. and Kohn, E. C. (1997) Invasion and metastasis. In: Holland, J. F., Frei, E. III., Bast, R. C., Jr., Kufe, D. W., Morton, D. L., and Weichselbaum, R. R., eds. *Cancer Medicine* 4$^{th}$ Edition. Baltimore: Williams and Wilkins, p. 165–180.

March, J. (1977) Advanced Organic Chemistry. Reactions, Mechanisms, and Structure. 2nd Edition. McGraw-Hill, New York.

Mattes, M. J., Griffiths, G. L., Diril, H., Goldenberg, D. M., Ong, G. L., and Shih, L. B. (1994) Processing of antibody-radioisotope conjugates after binding to the surface of tumor cells. Cancer 73:787–793.

Mikkelsen, T., Yan, P.-S., Ho, K.-L., Sameni, M., Sloane, B. F., and Rosenblum, M. L. (1995) Immunolocalization of cathepsin B in human glioma: implications for tumor invasion and angiogenesis. *J. Neurosurg.* 83:285–290.

Milton, R. C., Milton, S. C., and Kent, S. B. (1992) Total chemical synthesis of a D15 enzyme: the enantiomers of HIV-1 protease show recirprocal chiral substrate specificity. *Science* 256:1403–1404.

Mori, K., Yoshida, K., Kayama, T., Kaise, N., Fukazawa, H., Kiso, Y., Kikuchi, K., Aizawa, A., and Abe K. (1993) Thyroxine 5-deiodinase in human brain tumors. *J. Clin. Endocrinol. Metab.* 77:1198–1202.

Moscatello, D. K., Holgado-Madruga, M., Godwin, A. K., Ramirez, G., Gunn, G., Zoltick, P. W., Biegel, J. A., Hayes, R. L., and Wong, A. J. (1995) Frequent expression of a mutant epidermal growth factor receptor in multiple human tumors. *Cancer Res.* 55:5536–5539.

Nahum, A. E. (1996) Microdosimetry and radiocurability: modelling targeted therapy with b-emitters. *Phys. Med Biol.* 41:1957–1972.

Novak-Hofer, I., Amstutz, H. P., Morgenthaler, J. J., and Schubiger, P. A. (1994) Internalization and degradation of monoclonal antibody chCE7 by human neuroblastoma cells. *Int. J. Cancer* 57:427–432.

O'Donoghue, J. A., Bardiés, M., and Wheldon, T. E. (1995) Relationships between tumor size and curability for uniformly targeted radiotherapy with beta-emitting radionuclides. *J. Nucl. Med* 36:1902–1909.

O'Donoghue, J. A. (1996) Optimal therapeutic strategies for radioimmunotherapy. *Recent Results Cancer Res.* 141: 77–99.

Pittman, R. C., Carew, T. E., Glass, C. K., Green, S. R., Taylor, C. A., Jr., and Attie, A. D. (1983) A radioiodinated, intracellularly trapped ligand for determining the sites of plasma protein degradation in vivo. *Biochem J* 212: 791–800.

Press, O. W., DeSantes, K., Anderson, S. K., and Geissler, F. (1990) Inhibition of catabolism of radiolabeled antibodies by tumor cells using lysosomotropic amines and carboxylic ionophores. *Cancer Res.* 50:1243–1250.

Press, O. W., Howell-Clark, J., Anderson, S., and Bernstein, I. (1994) Retention of B-cell-specific monoclonal antibodies by human lymphoma cells. *Blood* 83:1390–1397.

Press, O. W., Eary, J. F., Appelbaum, F. R., Martin, P. J., Nelp, W. B., Glenn, S., Fisher, D. R., Porter, B., Matthews, D. C., Gooley, T., and Bernstein, I. D. (1995) Phase II trial of $^{131}$I-B1 (anti-CD20) antibody therapy with autologous stem cell transplantation for relapsed B cell lymphomas. *Lancet* 346:336–340.

Press, O. W., Shan D., Howell-Clark, J., Eary, J., Appelbaum, F. R., Matthews, D., King, D. J., Haines, A. M. R., Hamann, P., Hinman, L., Schochat, D., and Bernstein, I. D. (1996) Comparative metabolism and retention of iodine-125, yttrium-90, and indium-111 radioimmunoconjugates by cancer cells. *Cancer Res.* 56:2123–2129.

Reijngould, D. J. and Tager, J. M. (1977) The permeability properties of the lysosomal membrane. *Biochim. Biophys. Acta* 472:419–439.

Reist, C. J., Archer, G. E., Kurpad, S. N., Wikstrand, C. J., Vaidyanathan, G., Willingham, M. C., Moscatello, D. K., Wong, A. J., Bigner, D. D., and Zalutsky, M. R. (1995) Tumor-specific anti-epidermal growth factor receptor variant III monoclonal antibodies: use of the tyramine-cellobiose radioiodination method enhances cellular retention and uptake in tumor xenografts. *Cancer Res.* 55:4375–4382.

Reist, C. J., Garg, P. K., Alston, K. L., Bigner, D. D., and Zalutsky, M. R. (1996) Radioiodination of internalizing monoclonal antibodies using N-succinimidyl 5-iodo-3-pyridinecarboxylate. *Cancer Res.* 56:4970–4977.

Reist, C. J., Batra, S. K., Pegram, C. N., Bigner, D. D. and Zalutsky, M. R. (1997) In vitro and in vivo behavior of radiolabeled chimeric anti-EGFRvIII monoclonal antibody: comparison with its murine parent. *Nucl. Med Biol.* 24:639–647.

Rempel, S. A., Rosenblum, M. L., Mikkelsen, T., Yan, P.-S., Ellis, K. D., Golembieski, W. A., Sameni, M., Rozhin, J., Ziegler, G., and Sloane, B. F. (1994) Cathepsin B expression and localization in glioma progression and invasion. *Cancer Res.* 54:6027–6031.

Rogers, B. E., Anderson, C. J., Connett, J. M., Guo, L. W., Edwards, W. B., Sherman, E. L. C., Zinn, K. R., and Welch, M. J. (1996) Comparison of four bifunctional chelates for radiolabeling monoclonal antibodies with copper radio-isotopes: biodistribution and metabolism. *Bioconjugate Chem.* 7:511522.

Sautter-Bihl, M.-L., Herbold, G., and Bihl, H. (1996) Minimal residual disease: a target for radioimmunotherapy with $^{131}$I-labeled monoclonal antibodies? Some dosimetric considerations. *Recent Results Cancer Res.* 141:67–75.

Schold, S. C. Jr., Zalutsky, M. R., Coleman, R. E., Glantz, M. J., Friedman, A. H., Jaszczak, R. J., Bigner, S. H. and Bigner, D. D. (1993) Distribution and dosimety of 1–123-labeled monoclonal antibody 81C6 in patients with anaplastic glioma. *Invest. Radiol.* 28:488–496.

Schuster, J. M., Garg, P. K., Bigner, D. D. and Zalutsky, M. R. (1991) Improved therapeutic efficacy of a monoclonal antibody radioiodinated using N-succinimidyl-3-(tri-n-butylstannyl)benzoate. *Cancer Res.* 51:4164–4169.

Schwarz, U. P., Plascjak, P., Beitzel, M. P., Gansow, O. A., Eckelman, W. C., and Waldmann, T. A. (1998) Preparation of $^{211}$At-labeled humanized anti-Tac using $^{211}$At produced in disposable internal and external bismuth targets. *Nucl. Med. Biol.* 25:89–93.

Sharkey, R. M., Behr, T. M., Mattes, M. J., Stein, R., Griffiths, G. L., Shih, L. B., Hansen, H. J., Blumenthal, R. D., Dunn, R. M., Juweid, M. E., and Goldenberg, D. M. (1997a) Advantage of residualizing radiolabels for an internalizing antibody against the B-cell lymphoma antigen, CD22. *Cancer Immunol. Immunother.* 44:179–188.

Sivaparvathi, M., Sawaya, R., Wang, S. W., Rayford, A., Yamamoto, M., Liotta, L. A., Nicolson, G. L., and Rao, J. S. (1995) Overexpression and localization of cathepsin B during the progression of human gliomas. *Clin. Exp. Metastasis* 13:49–56.

Smith, M. F., Jaszczak, R. J., and Wang, H. (1997a) Lead and tungsten pinhole inserts for I-131 SPECT tumor imaging: experimental measurements and photon transport simulations. *IEEE Trans. Nucl. Sci.* 44:74–82.

Smith, M. F., Jaszczak, R. J., and Wang, H. (1997b) Pinhole aperture design for $^{131}$I tumor imaging. *IEEE Trans. Nucl. Sci.* 44:1154–1160.

Staros, J. V., Wright, R. W., and Swingle, D. M. (1986) Enhancement by N-hydroxysulfosuccinimide of water-soluble carbodiimide coupling reactions. *Anal. Biochem.* 156:220–222.

Stein, R., Goldenberg, D. M., Thorpe, S. R., Basu, A., and Mattes, M. J. (1995) Effects of radiolabeling monoclonal antibodies with a residualizing iodine radiolabel on the accretion of radioisotope in tumors. *Cancer Res.* 55:31323139.

Stein, R., Goldenberg, D. M., Thorpe, S. R., and Mattes, M. J. (1997) Advantage of a residualizing iodine label for radioimmunotherapy of xenografts of human non-small-cell carcinoma of the lung. *J. Nucl. Med* 38:391–395.

Stein. R., Govindan, S. V., Mattes, M. J., Griffiths, G. L., Hansen, H. J., and Goldenberg, D. M. (1998) A nonmetabolizable DTPA-peptide (DPEP) approach for production of a residualizing iodine radiolabel for targeting human lung cancer xenografts. Proc. Am. Assoc. Cancer Res. 39:380.

Strickland, D. K., Vaidyanathan, G., and Zalutsky, M. R. (1994) Cytotoxicity of alpha-particle-emitting m-[$^{211}$At]astatobenzylguanidine on human neuroblastoma cells. *Cancer Res.* 54:5414–5419.

Thorpe, S. R., Baynes, J. W., and Chroneos, Z. C. (1993) The design and application of residualizing labels for studies of protein catabolism. *FASEB J.,* 7:399–405.

Tjandra, J. J., Ramadi, L., and McKenzie, I. F. (1990) Development of hyman anti-murine antibody (HAMA) response in patients. *Immunol. Cell Biol.* 68:367–376.

Turkington, T. G., Zalutsky, M. R., Jaszczak, R. J., Garg, P., Vaidyanathan, G., and Coleman, R. E. (1993) Measuring astatine-211 distributions with SPECT. *Phys. Med Biol.* 38:1121–1130.

Vaidyanathan, G. and Zalutsky, M. R. (1997) Fluorine-18 labeled [Nle$^4$,D-Phe$^7$]-α-MSH, an α-melanocyte stimulating hormone analogue. *Nucl. Med Biol.* 24:171–178.

van der Jagt, R. H. C., Badger, C. C., Appelbaum, F. R., Press, O. W., Matthews, D. C., Eary, J. F., Krohn, K. A., and Bernstein, I. D. (1992) Localization of radiolabeled antimyeloid antibodies in a human acute leukemia xenograft tumor model. *Cancer Res.* 52:89–94.

Visser, T. J., Kaptein, E., Terpstra, O. T., and Krenning, E. P. (1988) Deiodination of thyroid hormone by human liver. *J. Clin. Endocrinol. Metab.* 67:17–24.

Wikstrand, C. J., Hale, L. P., Batra, S. K., Hill, M. L., Humphrey, P. A., Kurpad, S. N., McLendon, R. E., Moscatello, D., Pegram, C. N., Reist, C. J., Traweek, T., Wong, A. J., Zalutsky, M. R., and Bigner, D. D. (1995) Monoclonal antibodies against EGFRvIII are tumor specific and react with breast and lung carcinomas and malignant gliomas. *Cancer Res.* 55:3140–3148.

Wikstrand, C. J., McLendon, R. E., Friedman, A. H., and Bigner, D. D. (1997) Cell surface localization and density of the tumor-associated variant of the epidermal growth factor receptor, EGFRvIII. *Cancer Res.* 57:4130–4140.

Wong, A. J., Ruppert, J. M., Bigner, S. H., Grzeschik, C. H., Humphrey, P. A., Bigner, D. S., and Vogelstein, B. (1992) Structural alterations of the epidermal growth factor receptor gene in human gliomas. *Proc. Natl. Acad. Sci. USA* 89:2965–2969.

Wu, C., Jagoda, E., Brechbiel, M., Webber, K. O., Pastan, I., Gansow, O., and Eckelman, W. C. (1997) Biodistribution and catabolism of Ga-67-labeled anti-Tac dsFv fragment. *Bioconjugate Chem.* 8:365–369.

Xu, F. J., Yu, Y. H., Bae, D. S., Zhao, X.-G., Slade, S. K., Boyer, C. M., Bast, Jr., R. C. and Zalutsky, M. R. (1997) Radioiodinated antibody targeting of the HER-2/neu oncoprotein. *Nucl. Med Biol.* 24:451–459.

Zalutsky, M. R. and Narula, A. S. (1987) A method for the radiohalogenation of proteins resulting in decreased thyroid uptake of radioiodine. *Int. J. Radiat. Appl. Instrum.* [Part A] 38:1051–1055.

Zalutsky, M. R., and Narula, A. S. (1988) Astatination of proteins using an N-succinimidyl tri-n-butylstannyl benzoate intermediate. *Appl. Radiat. Isotop.* 39:227–232.

Zalutsky, M. R., Garg, P. K., Friedman, H. S. and Bigner, D. D. (1989b) Labeling monoclonal antibodies and F(ab')$_2$ fragments with the alpha particle emitting nuclide astatine-211: preservation of immunoreactivity and in vivo localizing capacity. *Proc. Natl. Acad. Sci. USA* 86:7149–7153.

Zalutsky, M. R., McLendon, R. E., Garg, P. K., Archer, G. E., Schuster, J. M., and Bigner, D. D. (1994) Radioimmunotherapy of neoplastic meningitis in rats using an alpha-particle-emitting immunoconjugate. *Cancer Res.* 54:47194725.

Zalutsky, M. R., Schuster, J. M., Garg, P. K., Archer, Jr., G. E., Dewhirst, M. W., and Bigner, D. D. (1996) Two approaches for enhancing radioimmunotherapy: alpha emitters and hyperthermia. Recent Results *Cancer Res.* 141:101–122.

Zalutsky, M. R., Stabin, M., Larsen, R. H. and Bigner, D. D. (1997) Tissue distribution and radiation dosimetry of astatine-211-labeled chimeric 81C6, an α-particle emitting immunoconjugate. *Nucl. Med Biol.* 24:255–262.

Zhu, H., Baxter, L. T., and Jain, R. K. (1997) Potential and limitations of radioimmunodetection and radioimmunotherapy with monoclonal antibodies. *J Nucl. Med* 38:731–741.

I claim:

1. A composition for selectively internally labeling a target cell, comprising
    a ligand which specifically binds to a surface antigen of a target cell and is internalized by the cell, wherein the ligand is selected from the group consisting of (1) an antibody (2) a fragment of an antibody and (3) a synthetic polypeptide;
    an oligopeptide which comprises at least one positively-charged amino acid residue and at least one D-amino acid residue, wherein the oligopeptide does not comprise two or more contiguous L-amino acids, wherein the oligopeptide comprises two non-contiguous L-amino acids separated from one another by one or more positively-charged D-amino acids, and wherein the oligopeptide is covalently bound to the ligand; wherein the oligopeptide does not specifically bind to the surface antigen; and
    a label which is covalently bound to the oligopeptide.

2. The composition of claim 1, wherein the label is a moiety of formula (II):

wherein X is a moiety selected from the group consisting of an amino, carboxyl, or sulfhydryl moiety, and wherein X forms a covalent linkage with the oligopeptide;

wherein Y is selected from the group consisting of C and N; and wherein Z is selected from the group consisting of F, Br, I, At, and M(Alk)$_3$; wherein M is selected from the group consisting of Si, Sn, and Hg; wherein Alk is selected from the group consisting of methyl, ethyl, propyl, butyl, pentyl, and hexyl.

3. The composition of claim 1, wherein the label is selected from the group consisting of 5-iodo-3-pyridinecarboxylate, 3-iodobenzoate, 3-(tri-n-butylstannyl)benzoate, 5-(tri-n-butylstannyl)-3-pyridinecarboxylate, and 5-astato-3-pyridinecarboxylate, 3-iodoaniline, 4-iodoaniline, 3-astatoaniline, 4-astatoaniline, 3-tributylstannylaniline, and 4-tributylstannylaniline.

4. The composition of claim 1, wherein the ligand is an antibody and wherein the antibody is a monoclonal antibody.

5. The composition of claim 1, wherein the ligand is an antibody and wherein the antibody is an interspecies recombinant antibody.

6. The composition of claim 1, wherein the ligand is an antibody and wherein the antibody is a humanized antibody.

7. The composition of claim 1, wherein the target cell is a tumor cell.

8. The composition of claim 1, wherein the ligand selectively binds to EGFRvIII.

9. The composition of claim 8, wherein the ligand is an antibody and wherein the antibody is a monoclonal antibody that specifically binds to EGFRvIII.

10. A composition for selectively internally labeling a target cell, comprising:
 a ligand which specifically binds to a surface antigen of a target cell and is internalized by the cell wherein the ligand is selected from the group consisting of (1) an antibody, (2) a fragment of an antibody, and (3) a synthetic polypeptide;
 an oligopeptide which comprises at least one positively-charged amino acid residue and at least one D-amino acid residue, wherein the at least one D-amino acid residue is D-Tyr, wherein the oligopeptide does not comprise two or more contiguous L-amino acids, wherein the oligopeptide is covalently bound to the ligand, and wherein the oligopeptide does not specifically bind to the surface antigen; and
 a label which is covalently bound to the oligopeptide.

11. The composition of claim 10, wherein the oligopeptide additionally comprises D-Arg.

12. The composition of claim 10, wherein the oligopeptide additionally comprises at least three D-Arg residues.

13. The composition of claim 1, wherein the oligopeptide comprises D-Lys.

14. The composition of claim 13, wherein the oligopeptide additionally comprises D-Arg.

15. The composition of claim 13 wherein the oligopeptide additionally comprises at least three D-Arg residues.

16. The composition of claim 1, wherein the label comprises a radionuclide.

17. The composition of claim 7, wherein the label comprises a radionuclide.

18. The composition of claim 16, wherein the radionuclide is an alpha, beta, or gamma emitter.

19. The composition of claim 16, wherein the radionuclide is selected from the group consisting of $^{18}$F, $^{75}$Br, $^{76}$Br, $^{77}$Br, $^{123}$I, $^{124}$I, $^{125}$I, $^{131}$I, and $^{211}$At.

20. The composition of claim 1, wherein the label is fluorescent.

21. The composition of claim 1, wherein the oligopeptide comprises at least two positively-charged amino acids.

22. The composition of claim 1, wherein the ligand is a fragment of an antibody comprising a portion of an immunoglobulin light chain variable region and a portion of an immunoglobulin heavy chain variable region.

23. The composition of claim 1, wherein the ligand is a single chain Fv fragment of an antibody.

24. The composition of claim 1, wherein the ligand comprises a single chain Fv fragment of an antibody.

25. The composition of claim 1, wherein the ligand is a synthetic polypeptide and the target cell is a tumor cell.

* * * * *